US006211438B1

(12) United States Patent
Anderson et al.

(10) Patent No.: US 6,211,438 B1
(45) Date of Patent: *Apr. 3, 2001

(54) HERBICIDE RESISTANCE IN PLANTS

(75) Inventors: Paul Curtis Anderson, Minneapolis; Kenneth A. Hibberd, Falcon Heights, both of MN (US)

(73) Assignee: MGI Pharma, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/947,249

(22) Filed: Sep. 18, 1992

Related U.S. Application Data

(63) Continuation of application No. 07/592,420, filed on Oct. 3, 1990, now Pat. No. 5,304,732, which is a continuation of application No. 06/900,960, filed on Aug. 28, 1986, now abandoned, which is a continuation-in-part of application No. 06/639,321, filed on Aug. 10, 1984, now Pat. No. 4,761,373, which is a continuation-in-part of application No. 06/586,802, filed on Mar. 6, 1984, now abandoned.

(51) Int. Cl.$^7$ .............................. A01H 1/06; A01H 5/00; A01H 5/10

(52) U.S. Cl. .................... 800/300; 800/270; 800/320; 800/320.1; 800/320.2; 800/320.3

(58) Field of Search ................................. 800/200, 235, 800/250, 270, 300, 320, 320.1, 320.2, 320.3

(56) References Cited

U.S. PATENT DOCUMENTS

| | | | |
|---|---|---|---|
| 4,127,405 | 11/1978 | Levitt | 71/93 |
| 4,169,719 | 10/1979 | Levitt | 71/92 |
| 4,190,432 | 2/1980 | Levitt | 71/93 |
| 4,214,890 | 7/1980 | Levitt | 71/90 |
| 4,221,585 | 9/1980 | Levitt | 71/92 |
| 4,225,337 | 9/1980 | Levitt | 71/93 |
| 4,231,784 | 11/1980 | Levitt | 71/92 |
| 4,257,802 | 3/1981 | Levitt | 71/93 |
| 4,293,330 | 10/1981 | Levitt | 71/94 |
| 4,302,241 | 11/1981 | Levitt | 71/92 |
| 4,310,346 | 1/1982 | Levitt | 71/92 |
| 4,339,266 | 7/1982 | Levitt | 71/92 |
| 4,339,267 | 7/1982 | Levitt | 71/92 |
| 4,342,587 | 8/1982 | Levitt | 71/92 |
| 4,348,219 | 9/1982 | Levitt | 71/92 |
| 4,368,067 | 1/1983 | Budzinski | 71/92 |
| 4,369,058 | 1/1983 | Levitt | 71/92 |
| 4,369,320 | 1/1983 | Levitt | 544/320 |
| 4,370,479 | 1/1983 | Levitt | 544/278 |
| 4,370,480 | 1/1983 | Levitt | 544/320 |
| 4,371,391 | 2/1983 | Levitt | 71/93 |
| 4,372,778 | 2/1983 | Levitt | 71/94 |
| 4,378,991 | 4/1983 | Levitt | 71/93 |
| 4,383,113 | 5/1983 | Levitt | 544/211 |
| 4,391,627 | 7/1983 | Levitt | 71/90 |
| 4,394,506 | 7/1983 | Levitt | 544/321 |
| 4,398,939 | 8/1983 | Levitt | 71/90 |
| 4,417,917 | 11/1983 | Levitt | 71/93 |
| 4,424,073 | 1/1984 | Levitt | 71/92 |
| 4,435,206 | 3/1984 | Levitt | 71/92 |
| 4,443,971 | 4/1984 | Chaleff et al. | 47/58 |
| 4,535,060 | 8/1985 | Comai | 435/172.3 |
| 4,666,844 | 5/1987 | Cheng | 435/240 |
| 4,757,011 * | 7/1988 | Chaleff et al. | 435/172.1 |
| 4,761,373 | 8/1988 | Anderson et al. | 435/172.3 |
| 4,774,381 | 9/1988 | Chaleff et al. | 800/230 |
| 5,013,659 | 5/1991 | Bedbrook et al. | 435/172.3 |
| 5,145,777 | 9/1992 | Goodman et al. | 435/172.3 |

FOREIGN PATENT DOCUMENTS

| | | | |
|---|---|---|---|
| 81103638 | 12/1981 | (EP) | C07D/401/04 |
| 81103639 | 12/1981 | (EP) | A01N/43/50 |
| 83306903 | 8/1984 | (EP) | C12N/15/00 |
| 84113656 | 5/1985 | (EP) | C07D/487/04 |
| 85101422 | 9/1985 | (EP) | C12N/15/00 |
| 85301188 | 9/1985 | (EP) | C12N/15/00 |

OTHER PUBLICATIONS

WP Anderson (1977) Weed Science: Principles pp. 500–501.*
F Meins Jr (1983) Ann Rev Plant Physiol 34:327–346.*
J Reinert (1973) In: Plant tissue and cell culture, HE Street, ed, pp. 348–353.*
SH Mantell et al (1985) Principles of Plant Biotechnology pp. 120.*
Yamada, Y. and Loh, W.H., Rice, In: Handbook Pl. Cell Cult., Ammirato et al. (eds.), 3: 151–170 (1984).
Kaur–Sawhney, R.L. and Galston, A.W., Oats, In: Handbook Pl. Cell Cult., Sharp, et al. (eds.), 2: 92–107 (1984).
Rangan, T.S. and Vasil, I.K., Millets, In: Handbook Pl. Cell Cult., Ammirato, et al. (eds.), 3: 126–150 (1984).
Nadar, H.M., et al., Fine Structure of Sugarcane (Saccharum sp.) Callus and the Role of Auxin in Embryogenesis, Crop Sci. 18: 210–216 (1978).
Rangan, T.S., Pineapple, In: Handbook Pl. Cell Cult., Ammirato, et al. (eds.), 3: 373–382 (1984).
Novak, F.J., et al., Allium, In: Handbook Pl. Cell Cult., Evans et al. (eds.), 4: 419–456 (1986).
Ahloowalia, B.S., Forage Grasses, In: Handbook Pl. Cell Cult., Ammirato, et al. (eds.), 3: 91–125 (1984).

(List continued on next page.)

*Primary Examiner*—David T. Fox
(74) *Attorney, Agent, or Firm*—Pennie & Edmonds LLP

(57) ABSTRACT

This invention is directed to the production of plants, plant tissues and seeds which are resistant to inhibition by an herbicide which normally inhibits the growth and development of those plants, plant tissues and plant seeds. In particular this invention is directed to altered acetohydroxyacid synthase enzymes which are resistant to inhibition by herbicides which normally inhibit the activity of the synthase before such alteration. This invention further relates to genes encoding such enzymes, and to processes for utilizing these novel genes and enzymes. Further products of the invention include plants, plant tissues and seeds which exhibit resistance to such herbicides resulting from expression of genes encoding herbicide resistant acetohydroxyacid synthase enzyme.

64 Claims, 4 Drawing Sheets

OTHER PUBLICATIONS

Flick, C.E., et al., Organogenesis, In: Handbook Pl. Cell Cult., Evans, et al. (eds.), 1: 43–81 (1983).

Ammirato, P.V., Embryogenesis, In: Handbook Pl. Cell Cult., Evans et al. (eds.), 1: 82–123 (1983).

Reisch, B., Genetic Variability in Regenerated Plants, In: Handbook Pl. Cell Cult., Evans, et al. (eds.), 748–769 (1983).

Evans, D.A. and Sharp, W.R., Somaclonal And Gametoclonal Variation, In: Handbook Pl. Cell Cult., Evans et al. (eds.), 4: 97–132 (1986).

Gamborg, O.L. and Shyluk, J.P., *Nutrition, Media and Characteristics of Plant Cell and Tissue Cultures,* In: Plant Tissue Culture, Thorpe (ed.), 21–44 (1981).

Evans, D.A. and Flick, C.E., Growth and Behavior of Cell Cultures: Embryogenesis and Organogenesis, In: Plant Tissue Culture, Thorpe (ed.), 45–113 (1981).

Singh, B.K., et al., Production of a Monocot Specific Monoclonal Antibody Against Acetohydroxyacid Synthase and Its Use In the Purification and Characterization of the Enzyme, Proc. Natl. Acad. Sci. 88: 4572–4576 (1991).

Chaleff and Ray, "Herbicide–Resistant Mutants from Tobacco Cell Cultures," Science 223: 1148–1151 (1984).

Meredith and Carlson, "Herbicide Resistance in Plant Cell Cultures," in *Herbicide Resistance in Plants,* Lebaron and Gressel (eds.), 1982, John Wiley and Sons, New York, pp. 275–291.

Chaleff and Mauvais, "Acetolactate Synthase in the Site of Action of Two Sulfonylurea Herbicides in Higher Plants," Science 224: 1443–1445 (1984).

Green and Donovan, "Effects of Aspartate–derived Amino Acids and Aminoethyl Cysteine on Growth of Excised Mature Embryos of Maize," Crop Sci 20: 358–362 (1980).

Gressel, "Biotechnologically Conferring Herbicide Resistance in Crops: The Present Realities," In *Molecular Form and Function of the Plant Genome,* L. van Vloten–Doting, (ed.), 1985, Plenum Press, New York, pp. 489–504.

Chih–Ching et al., "The N6 Medium and Its Applications to Anther Culture of Cereal Crops," In *Proceedings of Symposium of Plant Tissue Culture,* May, 1978, Science Press, Peking, pp. 43–50.

Murashige and Skoog, "A Revised Medium for Rapid Growth and Bio Assays with Tobacco Cultures," Physiol. Plantarum 15: 473–497 (1962).

Yamada, "Tissue Culture Studies on Cereals," in *Applied and Fundamental Aspects of Plant Cell, Tissue, and Organ Culture,* J. Reinert and Y.P.S. Bajaj (eds.), Springer–Verlag, 1977, Berlin, pp. 144–159.

Green and Rhodes, "Plant Regeneration in Tissue Cultures of Maize," In *Maize for Biological Research,* W.F. Sheridan (ed.), Plant Molecular Biology Association, Charlottesville, VA, 1982, pp. 367–372.

Gengenbach et al., "Inheritance of Selected Pathotoxin Resistance in Maize Plants Regenerated from Cell Cultures," Proc. Natl. Acad. Sci. U.S.A. 74: 5113–5117 (1977).

Hibberd and Green, "Inheritance and Expression of Lysine Plus Threonine Resistance Selected in Maize Tissue Culture," Proc. Natl. Acad. Sci. U.S.A. 79: 559–563 (1982).

Green et al., "Tissue Cultures of Maize (*Zea mays* L.): Initiation, Maintenance, and Organic Growth Factors," Crop Sci. 14: 54–58 (1974).

Radin and Carlson, "Herbicide—tolerant Tobacco Mutants Selected In Situ and Recovered Via Regeneration From Cell Culture," Genet. Res. Camb. 32: 85–89 (1978).

Singer and McDaniel, "Selection of Amitrole Tolerant Tobacco Calli and the Expression of This Tolerance in Regenerated Plants and Progeny," Theor. Appl. Genet. 67: 427–432 (1984).

Miller and Hughes, "Selection of Paraquat–Resistant Variants of Tobacco From Cell Cultures," In Vitro 16(12): 1085–1091 (1980).

Smith et al., "Mutations Affecting the Formation of Acetohydroxyacid Synthase II in *Escherichia Coli* K–12," Molec. Gen. Genet. 169: 299–314 (1979).

Green and Phillips, "Potential Selection System for Mutants with Increased Lysine, Threonine, and Methionine in Cereal Crops," Crop Sci. 14:827–830 (1974).

Comai et al., "An Altered aroA Gene Product Confers Resistance to the Herbicide Glyphosate," Science 221: 370–371 (1983).

Aviv and Galun, "Isolation of Tobacco Protoplasts in the Presence of Isopropyl N–Phenylcarbamate and Their Culture and Regeneration into Plants," Z. Pflanzenphysiol. Bd. 83: 267–273 (1977).

Barg and Umiel, "Development of Tobacco Seedlings and Callus Cultures in the Presence of Amitrole," Z. Pflanzenphysiol. Bd. 83: 437–447 (1977).

Sibi, "Heritable Epigenic Variations from in vitro Tissue Culture of *Lycopersicon esculentum* (var.) Monalbo," Chapter 17 in *Variability in Plants Regenerated from Tissue Culture,* E.D. Earle and Y. Demarly (eds.), Praeger Publ., New York, 1982, pp. 228–244.

Gerhardt et al., Manual of Methods for General Bacteriology, American Society for Microbiology, Washington, D.C., 1981, pp. 224–227.

Shaner et al., "Imidazolinones. Potent Inhibitors of Acetohydroxyacid Synthase," Plant Physiol. 76: 545–546 (1984).

Ray, "Site of Action of Chlorsulfuron. Inhibition of Valine and Isoleucine Biosynthesis in Plants," Plant Physiol. 75: 827–831 (1984).

Hirschberg et al., "Molecular Basis of Herbicide Resistance in *Amaranthus hybridus,*" Science 222: 1346–1349 (1983).

Donn et al., "Herbicide–Resistant Alfalfa Cells: An Example of Gene Amplification in Plants," J. Mol. Appl. Genet. 2: 621–635 (1984).

Goodman et al., "Gene Transfer in Crop Improvement," Science 236: 48–54 (1987).

Duke, "Glyphosate," in *Herbicides: Chemistry, Degradation and Mode of Action* (2nd ed.), P.C. Kearney and D.D. Kaufman (eds.), 1988, vol. 3, pp. 1–59.

Jawarski, "Chloroacetamides," in *Herbicides: Chemistry, Degradation and Mode of Action* (2nd ed.), P.C. Kearney and D.D. Kaufman (eds.), vol. 1, pp. 349–376 (1975).

Fang, "Thiocarbamates," in *Herbicides: Chemistry, Degradation and Mode of Action* (2nd ed.), P.C. Kearney and D.D. Kaufman (eds.), vol. 1, pp. 323–348 (1975).

Anderson et al., "Cell Culture Selection of Herbicide Tolerant Corn," American Society of Agronomy (abstract), Plant Physiol. 77 (Suppl.4), 142 (1985).

Zelitch and Berlyn, "Altered Glycine Decarboxylation Inhibitors in Isonicotinic Acid Hydrazide Resistant Mutant Callus Lines and in Regenerated Plants and Seed Progeny," Plant Physiol. 69: 198–204 (1982).

Merrick and Collin, "Selection for Asulam Resistance in Tissue Cultures of Celery," Plant Sci. Lett. 20: 291–296 (1981).

Ray, "Sulfonylurea Herbicides as Inhibitors of Amino Acid Biosynthesis in Plants," Trends Biochem. Sci. 11(4): 180–183 (1986).

Keil and Chaleff, "Genetic Characterization of Hydroxyurea–Resistant Mutants Obtained from Cell Cultures of *Nicotiana tobacum*," Mol. Gen. Genet. 192: 218–224 (1983).

Müller, "Genetic Analysis of Nitrate Reductase–Deficient Tobacco Plants Regenerated from Mutant Cells," Mol. Gen. Genet. 192: 275–281 (1983).

Vasil, "Plant Cell Culture and Somatic Cell Genetics of Cereals and Grasses," in *Plant Improvement and Somatic Cell Genetics,* I.K. Vasil, W.R. Scowcroft and K.J. Frey (eds.), 1982, pp. 179–203.

Haughn and Somerville, "Sulfonylurea–resistant Mutants of *Arabidopsis thaliana*," Molec. Gen. Genet. 204: 430–434 (1986).

Bryan, "Synthesis of the Aspartate Family and Branched––Chain Amino Acids," in *The Biochemistry of Plants: A Comprehensive Treatise,* B.J. Miflin (ed.), Academic Press, New York, 1980, pp. 403–452.

Carlson, "Methionine Sulfoximine–Resistant Mutants of Tobacco," Science 180: 1366–1368 (1973).

Chaleff and Carlson, "Somatic Cell Genetics of Higher Plants," Ann. Rev. Genet. 8: 267–278 (1974).

Maliga, "Isolation of Mutants from Cultured Plant Cells," in *Cell Genetics in Higher Plants,* 1976, D. Dudits et al. (eds.), Akademiai Kiado, Budapest, 1976, pp. 59–76.

Chaleff, "Further Characterization of Picloram–tolerant Mutants of *Nicotiana tobacum*," Theor. Appl. Genet. 58: 91–95 (1980).

Hughes, "Selection for Herbicide Resistance in *Handbook of Plant Cell Culture*," D.A. Evans et al. (eds.), vol. 1, MacMillan, New York, 1983, pp. 442–460.

Green and Phillips, "Plant Regeneration from Tissue Cultures of Maize," Crop Sci. 15: 471–421 (1975).

Chaleff et al., Proc. Natl. Acad. Sci. USA 75: 5140–5107 (1978).

Miller et al., In Vitro 16: 1085–1091 (1980).

Singer et al., Plant Physiol. 69: 1382–1386 (1982).

Thomas et al., Theor. Appl. Genet. 63: 169–176 (1982).

Chester L. Foy, Picloram and Related Compounds, in *Herbicides: Chemistry, Degradation and Mode of Action* (2nd ed.), P.C. Kearney and D.D. Kaufman eds., 1976, vol. 2, pp. 777–813.

Mason S. Carter, Amitrole, in *Herbicides: Chemistry, Degradation and Mode of Action* (2nd ed.), P.C. Kearney and D.D. Kaufman eds., 1975, vol. 1, pp. 377–398.

Ashton and Crafts, *Mode of Action of Herbicides* (2nd ed.), John Wiley & Sons (1981), pp. 180–200.

*Herbicide Handbook* (3rd ed.), Weed Science Society of America (1974), pp. 26–28, 47–50 and 299–302.

Alan Calderbank and Peter Slade, Diquat and Paraquat, in *Herbicides: Chemistry, Degradation and Mode of Action* (2nd ed.), P.C. Kearney and D.D. Kaufman eds., 1976, vol. 2, pp. 501–541.

Michael A. Loos, Pheynoxyalkanoic Acids, in *Herbicides: Chemistry, Degradation and Mode of Action* (2nd ed.), P.C. Kearney and D.D. Kaufman eds., 1975, vol. 1, pp. 61–101.

Stephen O. Duke, Glyphosate, in *Herbicides: Chemistry, Degradation and Mode of Action* (2nd ed.), P.C. Kearney and D.D. Kaufman eds., 1988, vol. 3, pp. 1–3, 26–59.

Nishi et al., Nature 219: 508–509 (1968).

Heyser et al., Plant Sci. Lett. 29: 175–182 (1983).

Bajaj et al., Phytomorphology 30: 290–294 (1980).

Sears et al., Crop Sci. 22: 546–550 (1982).

Chin et al., Ann. Bot. 41: 473–481 (1977).

Ahloowalia, Crop Sci. 22: 405–410 (1982).

Ahuja et al., Z. Pflanzenzüchtg. 89: 139–144 (1982).

Ozias–Akins et al., Protoplasma 110: 95–105 (1982).

McHughen, Ann. Bot. 51: 851–853 (1983).

Dale et al., Z. Pflanzenphysiol. Bd. 94: 65–77 (1979).

Gamborg et al., Plant Sci. Lett. 10: 67–74 (1977).

Cummings et al., Crop Sci. 16: 465–470 (1976).

Eapen et al., Plant Cell Tissue Organ Culture 1: 221–227 (1982).

Vasil et al., Amer. J. Bot. 68: 864–872 (1981).

* cited by examiner

HERBICIDE RESISTANCE IN PLANTS

CROSS-REFERENCE TO RELATED APPLICATIONS

This application is a continuation of application Ser. No. 07/592,420, filed Oct. 3, 1990, now U.S. Pat. No. 5,304,732, which is a continuation of application Ser. No. 06/900,960, filed Aug. 28, 1986, now abandoned, which is a continuation-in-part of application Ser. No. 639,321, filed Aug. 10, 1984, now U.S. Pat. No. 4,761,373, which in turn is a continuation-in-part of application Ser. No. 586,802, filed Mar. 6, 1984, now abandoned, all of which are incorporated herein by reference.

1. FIELD OF THE INVENTION

This invention relates to genes and enzymes which confer resistance to herbicides in plants, plant tissues and seeds. In particular, the invention involves agronomically important crops which are resistant to herbicides, and which genetically transmit this characteristic to their progeny.

2. BACKGROUND OF THE INVENTION

2.1. WEED CONTROL

The use of herbicides for controlling weeds or plants in crops has become almost a universal practice. The market for these herbicides approaches a billion dollars annually. Even with this extensive use, weed control remains a significant and costly problem for the farmer.

Present day herbicides used singly or in so-called tank mixes require good management to be effective. Time and method of application and stage of weed plant development are critical to getting good weed control with herbicides. Some weed species are simply resistant to today's herbicides. Therefore, the production of effective herbicides increases in importance every year, especially as other weeds are controlled and thus reduce competition. Application of large amounts of marginally effective herbicides on these weeds can result in a commitment to grow the same crop in subsequent years because of chemical persistence in the soil which prevents rotation with a crop sensitive to that herbicide.

Other herbicides, while not used directly to control weeds in field crops, are used as "total vegetation control agents" to entirely eliminate weeds in certain railroad and industrial situations. These herbicides may be deposited on areas where crops are planted by water run-off, or other natural means. Thus, in fields affected by run-off from land on which total vegetation control agents have been used, sensitive field crops may be killed or their growth seriously inhibited.

Herbicides with greater potency, broader weed spectrum and more rapid degradation in the soil would have a significant impact on these problems. Unfortunately, these compounds also have greater crop phytotoxicity. Crop hybrids or varieties with resistance to the compounds would provide an attractive solution by allowing the compounds to be used without risk of damage to the crop.

2.2. TISSUE CULTURE OF MAIZE

Irrespective of the plant species, there are a number of common features that apply to most tissue culture programs. The technique of cell and tissue culture has been widely developed, and much work has been done on growth, metabolism and differentiation of tissue culture of dicotyledons (Yamada, 1977, in Plant Cell, Tissue and Organ Culture, eds. Reinert and Bajaj, pp. 144–159, Springer-Verlag, Berlin). However, successful tissue culture studies with monocotyledons (e.g., the cereal crops such as maize, rice, wheat, barley, sorghum, oats, rye and millet) leading to plant regeneration are not as well documented as with dicotyledons. Success is frequently dependent on choosing donor tissues for culture initiation which come from plants of appropriate genotype as well as physiological and development states. Other features which are obviously also important include the organic and inorganic composition of the growth medium and the physical environment in which the cultures are grown.

In maize, the development of tissue cultures capable of plant regeneration was accomplished after the identification of appropriate genotypes and donor tissues (Green and Rhodes, 1982 in Maize for Biological Research, ed. W. F. Sheridan, pp. 367–371, Plant Molecular Biology Associates, Charlottesville, Va.). The first method developed which regenerated plants from tissue cultures of maize used immature embryos as donor tissues. With N6 or MS growth media (defined below in Section 6) and a synthetic auxin, such as 2,4-dichlorophenoxyacetic acid (2,4-D), tissue cultures develop rapidly from the scutellum of the embryos. The resulting cultures are developmentally heterogeneous and contain a variety of tissue types. Removal of the 2,4-D from the growth medium permits these cultures to produce large numbers of regenerated plants. Cultures of this type have proved capable of regenerating plants for up to three years.

Another donor tissue from which regenerable tissue cultures of maize have been initiated are immature tassels. This tissue is the male flower and as it matures it is responsible for pollen production. Immature embryos, inflorescences, and the few other tissues in cereals from which regenerating cultures have been initiated all have the common characteristic of juvenility. Regenerated plants obtained from tissue cultures are grown to maturity in a glasshouse, growth chamber, or field. The progeny seed produced in crosses with regenerated plants permits the evaluation of subsequent generations. The basic tissue culture methods developed for corn have been extended to many other cereal species.

An interesting development in recent years has been the occurrence of somatic embryogenesis in tissue cultures of maize. Somatic embryogenesis is the process where cells from callus, suspension, or protoplast cultures develop into complete embryos similar to zygotic embryos produced in seeds. It is now possible to reliably initiate cultures of corn which have two important characteristics. One is that the callus cultures are friable, meaning that they are soft and loose in texture. This property is important because cultures of this type exhibit rapid growth and it facilitates the initiation of suspension cell cultures. The other valuable attribute of these friable cultures is their ability to form very large numbers of somatic embryos. Microscopic examination reveals the presence of many small, organized structures on the surface of the callus. These structures are young somatic embryos at various developmental stages. These friable cultures will retain their embryogenic potential for as long as two years and have shown the capacity to produce extremely large numbers of somatic embryos.

The somatic embryos in these friable calli develop to maturity when the cultures are transferred to medium containing 5 to 6 percent sucrose and no hormones. After approximately two weeks of growth on this medium, many embryos have become quite mature. They germinate rapidly and grow into plants when placed on MS or N6 medium containing 2% sucrose. The plants are then established in soil and are grown to maturity.

It is now well-documented that a high level of genetic variability can be recovered from plant tissue culture. It is well documented that spontaneous genetic variability in cultured plant cells may be the result of mutation (Meredith and Carlson, 1982, in Herbicide Resistance in Plants, eds. Lebaron and Gressel, pp. 275–291, John Wiley and Sons, NY). The frequency of mutants can also be increased by the use of chemical or physical mutagens. Some of this variability is of agronomic importance. Mutants for disease resistance have been obtained in sugarcane for Fiji disease, early and late blight in potato, and southern corn leaf blight in maize. In rice, maize, and wheat considerable variability for traits inherited as single genes of plant breeding interest have been recovered, including time of seed set and maturation, seed color and development, plant height, plant morphology, and fertility.

Tissue cultures of maize have been used to recover mutants for disease resistance and amino acid overproduction as described below.

Texas male sterile cytoplasm (cms-T) genotypes of maize are susceptible to the pathotoxin produced by the fungus *Helminthosporium maydis* race T while normal cytoplasm (N) genotypes are resistant (Gengenbach et al., 1977, Proc. Natl. Acad. Sci. USA 74: 5113–5117). Similarly, tissue cultures obtained from cms-T genotypes are susceptible to the pathotoxin while N genotype cultures are resistant. The pathotoxin from *H. maydis* race T was used to select resistant cell lines from susceptible cms-T cultures using a sublethal enrichment selection procedure. After five cycles of increasing selection pressure, cell lines were recovered which were resistant to lethal levels of the pathotoxin. Plants regenerated from these cell lines also were resistant to the pathotoxin and were male-fertile. Genetic analysis of progeny obtained from resistant, male-fertile plants showed that both traits were maternally inherited. Infection of plants with *H. maydis* race T spores demonstrated that selection for pathotoxin resistance also resulted in resistance to the disease organism by plants.

Selection for resistance to growth inhibition by lysine plus threonine in equimolar concentrations (LT) in tissue cultures of maize yielded a stable resistant line, LT19 (Hibberd and Green, 1982, Proc. Natl. Acad. Sci. USA 79: 559–563). Genetic analysis of progeny of plants regenerated from LT19 showed that LT resistance was inherited as a single dominant nuclear gene. Tissue cultures initiated from resistant embryos required 5–10 times higher levels of LT to inhibit growth than did cultures from LT-sensitive embryos. LT resistance in LT19 was expressed as reduced sensitivity of root and shoot growth to the presence of LT. The free pool of threonine was increased 6 times in cultures initiated from immature embryos of LT-resistant plants, and 75–100 times in kernels homozygous for LT19, as compared to cultures and kernels from LT-sensitive embryos and plants, respectively. Overproduction of free threonine increased the total threonine content in homozygous LT19 kernels by 33–59%. The results demonstrate that LT resistance selected with tissue culture methods was heritable and was expressed in cultures, seedlings, and kernels.

2.3. MECHANISMS OF HERBICIDE RESISTANCE

There are three general mechanisms by which plants may be resistant to, or tolerant of, herbicides. These mechanisms include insensitivity at the site of action of the herbicide (usually an enzyme), rapid metabolism (conjugation or degradation) of the herbicide, or poor uptake and translocation of the herbicide. Altering the herbicide site of action from a sensitive to an insensitive form is the preferred method of conferring resistance on a sensitive plant species. This is because resistance of this nature is likely to be a dominant trait encoded by a single gene and is likely to encompass whole families of compounds that share a single site of action, not just individual chemicals. Therefore, detailed information concerning the biochemical site and mechanism of herbicide action is of great importance and can be applied in two ways. First, the information can be used to develop cell selection strategies for the efficient identification and isolation of appropriate herbicide resistant variants. Second, it is used to characterize the variant cell lines and regenerated plants that result from the selections.

2.4. HERBICIDE RESISTANCE SELECTION

Tissue culture methods have been used to select for resistance (or tolerance) using a variety of herbicides and plant species (see review by Meredith and Carlson, 1982, in Herbicide Resistance in Plants, eds. Lebaron and Gressel, pp. 275–291, John Wiley and Sons, NY). The results of these investigations can be separated into two categories based on whether or not herbicide tolerance was stably inherited and expressed in the progeny of plants regenerated from the selected resistant cultures. This criterion clearly establishes the mutant nature of the selected trait. A number of tissue culture studies have been conducted to select for tolerance to 2,4-dichlorophenoxyacetic acid (2,4-D) in carrot, tobacco and white clover, to amitrole in tobacco, to asulam in celery, and to paraquat in tobacco, in none of which was the mutant nature of the resistance trait established by genetic analysis. These studies have therefore provided little evidence demonstrating the feasibility of tissue culture selection methods to produce herbicide resistant mutant plants which transmit the trait to progeny which express the resistance.

Three studies are available, however, which provide evidence that tissue culture methods can be utilized to obtain herbicide resistant mutants. Tobacco selected for tolerance to bentazon and phenmedipham yielded resistant plants (Radin and Carlson, 1978, Genet. Res., Camb., 32: 85–90). Genetic analysis of progeny from regenerated plants yielded data in the F2 generation confirming a genetic basis for resistance in 8 bentazon and 2 phenmedipham selected lines. The F2 segregation ratios indicated single gene recessive mutations for most of the lines except two bentazon lines in which two genes were indicated.

Chaleff and Parsons (1978, Proc. Natl. Acad. Sci. USA 75: 5104–5107) used tissue culture selection methods to isolate picloram resistant mutants from tobacco suspension cultures. Plants were regenerated from six of seven resistant lines selected. Resistance to picloram was transmitted to progeny in four of these lines and was expressed in both plants and callus tissues. In all four cases, segregation ratios were those expected from dominant single-gene mutations. In additional genetic analysis two of these mutants were shown to be linked.

Tomato callus lines were selected for the ability to grow at paraquat concentrations lethal to wild-type cells (Thomas and Pratt, 1983, Theor. Appl. Genet. 63: 109–113). Diploid plants were regenerated from 9 of the 19 paraquat resistant callus lines isolated. New callus cultures were initiated from these regenerated plants and typically showed at least a 30 fold increase over wild-type in resistance to paraquat. Tests on callus lines initiated from sexual progeny of regenerated plants showed that the paraquat resistance phenotype of three lines resulted from dominant nuclear mutations. Paraquat spray experiments indicated that slight paraquat resistance was expressed at the plant level in only one of the resistant lines.

2.5. HERBICIDAL IMIDAZOLINONES

A broad selection of imidazolinones, particularly 2-(2-imidazolin-2-yl)pyridines and 2-(2-imidazolin-2-yl)quinolines, or derivatives thereof, exhibit herbicidal activity.

See, for example, European Patent Application 81 103638.1 naming Los as inventor and American Cyanamid Company as applicant, which application is incorporated herein by reference. Exemplary herbicides of particular interest described in this application are 2-(5-isopropyl-5-methyl-4-oxo-2-imidazolin-2-yl)nicotinic acid (AC 243,997), 2-(5-isopropyl-5-methyl-4-oxo-2-imidazolin-2-yl)3-quinolinecarboxylic acid (AC 252,214), [5-ethyl,2-(5-isopropyl-5-methyl-4-oxo-2-imidazolin-2-yl)nicotinic acid (AC 263,499), and acid addition salts thereof.

For purposes of reference in the present specification, the herbicides described in this Section 2.5, and structurally related herbicidal compounds, are collectively referred to as imidazolinones or the imidazolinone family of herbicides.

2.6. HERBICIDAL SULFONAMIDES

Certain sulfonamides exhibit general and selective herbicidal activity against plants. Such herbicidal sulfonamides are disclosed in at least the following issued United States Patents:

| | | |
|---|---|---|
| 4,435,206 | 4,370,480 | 4,302,241 |
| 4,424,073 | 4,370,479 | 4,293,330 |
| 4,417,917 | 4,369,320 | 4,257,802 |
| 4,398,939 | 4,369,058 | 4,231,784 |
| 4,394,506 | 4,368,067 | 4,225,337 |
| 4,391,627 | 4,348,219 | 4,221,585 |
| 4,383,113 | 4,342,587 | 4,214,890 |
| 4,378,991 | 4,339,267 | 4,190,432 |
| 4,372,778 | 4,339,266 | 4,169,719 |
| 4,371,391 | 4,310,346 | 4,127,405 |

All of such United States patents are incorporated herein by reference. One such herbicidal sulfonamide of particular interest is 2-chloro-N-[(4-methoxy-6-methyl-1,3,5-triazin-2-yl)aminocarbonyl] benzenesulfonamide, also known as chlorsulfuron.

Additional sulfonamides having herbicidal activity are described in European patent application 84 113656.7 of Gerwick et al., filed Nov. 12, 1984, which is incorporated herein by reference. This application describes herbicidal compounds which are referred to herein as 1,2,4-triazolo[1,5-a] pyrimidine-2-sulfonamides. One such compound of particular interest is 5,7-dimethyl-N-(2,6-dichlorophenyl)-1,2,4-triazolo[1,5-a]pyrimidine-2-sulfonamide, hereafter referred to as 567.

For purposes of reference in the present specification, the herbicides referred to in this Section 2.6, and structurally related herbicidal compounds, are collectively referred to as herbicidal sulfonamides.

3. SUMMARY OF THE INVENTION

This invention is directed to agronomically important plants, plant tissues, and plant seeds which are resistant to inhibition by an herbicide at concentrations which normally inhibit the growth and development of those plants, plant tissues and plant seeds. The present invention contemplates the introduction of herbicide resistance into any agronomically important crop including, but not limited to, certain dicotyledons, monocotyledons, and specifically cereal crops such as rice, maize, wheat, barley, sorghum, oats, rye, millet and the like.

In particular this invention is directed to processes for the production of plants, plant tissues, and plant seeds which contain an enzyme which is resistant to inhibition by an herbicide at a concentration which normally inhibits the activity of this enzyme before alteration. This enzyme, an altered acetohydroxyacid synthase (AHAS), confers resistance to certain herbicides in plants, plant tissues and seeds. This invention is also directed to processes and compositions for making and utilizing this altered enzyme, as well as the gene encoding the resistant enzyme. One particular embodiment of the present invention is directed to the production of an herbicide resistant cell line possessing an alteration at the primary site of action of an herbicide. The present invention utilizes cell culture technology to isolate, characterize and develop herbicide resistant maize lines which genetically transmit this herbicide resistance characteristic to their progeny.

The present invention also provides a method of generating plants, plant tissues and seeds from these resistant cell lines which contain a gene coding for an altered acetohydroxyacid synthase resistant to inhibition by an herbicide at a concentration which normally inhibits the activity of this enzyme before alteration.

Additionally, this invention relates to plants (and seeds and plant tissue cultures) which are selectively resistant to one herbicide at levels which normally inhibit the growth and development of the plants, and which are sensitive to inhibition by another herbicide. In particular, such plants may be selectively resistant to a 2-(2-imidazolin-2-yl) pyridine with sensitivity to a herbicidal sulfonamide or to a 1,2,4-triazolo[1,5-a] pyrimidine-2-sulfonamide, as defined herein. Alternate relative resistances and sensitivities to herbicides are also within the scope of this invention.

In the examples presented herein, a novel enzyme, an altered acetohydroxyacid synthase which is resistant to inhibition by certain imidazolinone and/or sulfonamide herbicides (at concentrations which normally inhibit the activity of the unaltered enzyme) is described. This enzyme confers resistance to the herbicides in plants, plant tissues and seeds. Maize genotypes expressing this altered AHAS are described. This maize genotype may be used with the imidazolinone or sulfonamide herbicides to effectively combat weed problems in maize production.

The present invention further contemplates that herbicide resistance to the compounds described herein may be conferred by a variety of other mechanisms. For example, resistance may be conferred by a gene coding for an enzyme which may be obtained from any source including, but not limited to, eukaryotic organisms, prokaryotic organisms, or it may be made in whole or part by chemical or enzymatic synthetic methods. Other mechanisms of resistance are discussed in Section 2.3 supra.

It is to be understood that the following detailed description presents a single embodiment of the invention. This embodiment relates to an alteration in a particular enzyme, acetohydroxyacid synthase, which renders plants, plant tissues and seeds resistant to certain imidazolinones, the herbicides for which resistance was selected. Unexpectedly, these plants, plant tissues and seeds were also found resistant to certain sulfonamide herbicides. Thus, the altered enzyme disclosed herein may confer resistance to a variety of herbicides which inhibit acetohydroxyacid synthase as their primary site of action.

4. BRIEF DESCRIPTION OF THE FIGURES

5. DETAILED DESCRIPTION OF ONE EMBODIMENT OF THE INVENTION

Figure 1:
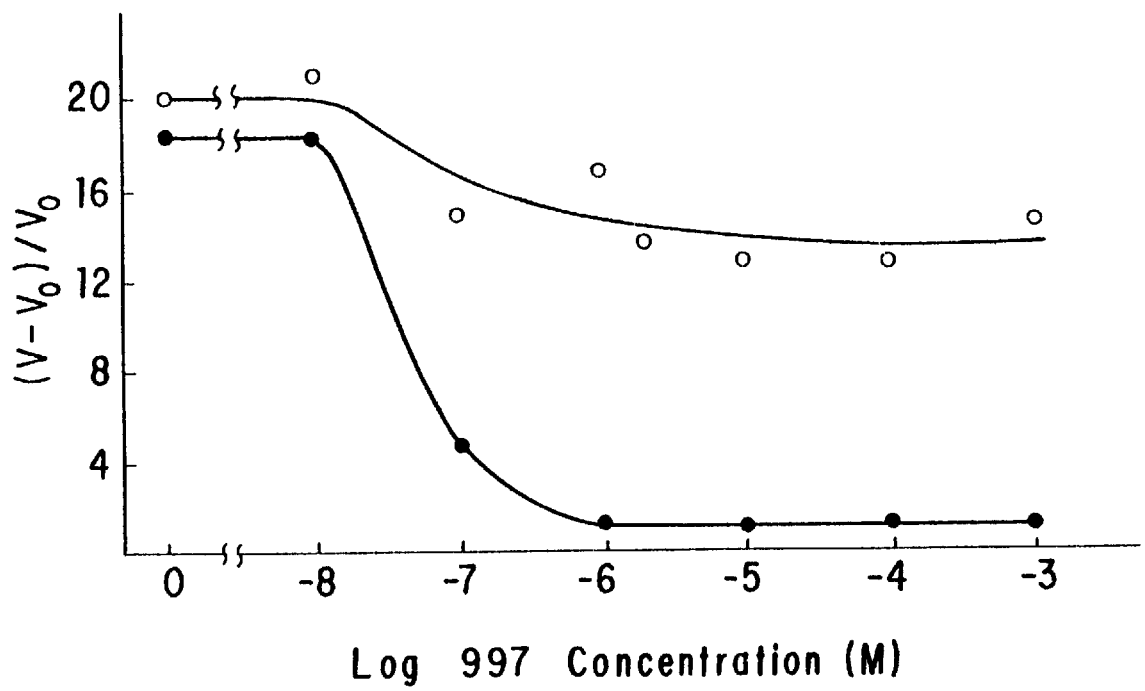
FIG. 1 shows the growth of maize cell suspension cultures as a function of AC 243,997 concentration with (open circles) or without (closed circles) media supplementation with 1.0 mM each of leucine, valine and isoleucine.

This embodiment of the invention relates to plants, plant tissues, and plant seeds which contain an enzyme which is resistant to inhibition by imidazolinone and/or sulfonamide herbicides. The enzyme is an altered acetohydroxyacid synthase which confers resistance to the above-mentioned herbicides in plants, plant tissues and seeds. Methods and compositions are provided for producing plants, plant tissues and seeds containing a gene coding for an altered AHAS. Also described are cell culture selection techniques to select for novel maize genotypes resistant to certain imidazolinone and/or sulfonamide herbicides. The production of these maize lines encompasses isolation, characterization, and development of these maize lines and regeneration of plants from these cultures which are resistant to the herbicides.

The method of this invention may be divided into the following areas for the purposes of description: (1) determination of the primary site of action of the imidazolinone family of herbicides; (2) characterization of the affects of the imidazolinone herbicides on maize cell cultures and the strategy for selection of herbicide resistant cell lines; (3) selection and characterization of herbicide resistant cell lines; (4) regeneration of herbicide resistant plants and production of seed; and (5) development of herbicide resistant commercial hybrid seed.

5.1. DETERMINATION OF THE PRIMARY SITE OF ACTION OF THE IMIDAZOLINONE FAMILY OF HERBICIDES

The biochemical site of action of the herbicides, including but not limited to the imidazolinone family and sulfonamide family of herbicides, in maize tissue is determined by first evaluating which general cell metabolic processes are affected by tissue exposure to the phytotoxic compounds. The specific site of action is then localized by in vitro evaluation of the individual reactions within the affected metabolic pathway or process.

The primary site of action may be determined by adding to tissue exposed to herbicide various products of the pathway(s) which is suspected to be affected by the herbicide. Those products which reverse the growth inhibitory effects of the herbicide indicate the pathway(s) affected by the herbicide.

5.2. CHARACTERIZATION OF THE EFFECTS OF THE IMIDAZOLINONE HERBICIDES ON PLANT CELL CULTURES AND STRATEGY FOR SELECTION OF HERBICIDE RESISTANT CELL LINES

Efficient selection of a desired herbicide resistant mutant using tissue culture techniques requires careful determination of selection conditions. These conditions are optimized to allow growth and accumulation of rare herbicide resistant cells in the culture while inhibiting the growth of the bulk of the cell population. The situation is complicated by the fact that the vitality of individual cells in a population is highly dependent on the vitality of neighboring cells.

Conditions under which cell cultures are exposed to the herbicides are determined by the characteristics of the interaction of the compounds with the tissue. Such factors as the accumulation of the compounds by cells in culture, and the persistence and stability of the compounds, both in the media and in the cells, need to be considered. Also important is whether the effects of the compounds can be readily reversed following their removal.

Aside from factors associated with the chemistry of the herbicidal compounds, their effects on culture viability and morphology need to be carefully evaluated. It is especially important to choose herbicide exposure conditions which have no impact on plant regeneration capability of cultures. Choice of herbicide exposure conditions is also influenced by whether the herbicide kills cells or simply inhibits cell divisions.

The choice of a selection protocol is dependent upon the considerations described supra. Either of the protocols briefly described below may be utilized in the selection procedure, although the present invention is not limited to these procedures. In the first protocol, finely divided cells in liquid suspension culture are exposed to high herbicide levels for brief periods of time. Surviving cells are then allowed to recover and accumulate and are then reexposed for subsequently longer periods of time. Alternatively, organized, partially differentiated cell cultures are grown and subcultured with continuous exposure to initially low herbicide levels. Herbicide concentrations are then gradually increased over several subculture intervals.

5.3. SELECTION AND CHARACTERIZATION OF RESISTANT CELL LINES

Selections are carried out until cells or tissue are recovered which are observed to be growing well in the presence of normally toxic herbicide levels. These cell "lines" are then repeatedly subcultured in the presence of herbicide and characterized. The amount of resistance which has been obtained is determined by comparing the growth of these cell lines with the growth of unselected cells or tissue in the presence of various herbicide concentrations. Stability of the herbicide resistance trait of the cultured cells may be evaluated by simply growing the selected cell lines in the absence of herbicide for various periods of time and then analyzing growth after reexposing the tissue to herbicide.

In the present invention, cell lines which are resistant by virtue of having an altered herbicide site of action are of primary interest. Cell lines may also be tested for resistance to herbicides structurally related to the selection agent. The resistant cell lines may also be evaluated using in vitro chemical studies to verify that the site of action of the herbicide is altered to a form which is less sensitive.

5.4. PLANT REGENERATION AND PRODUCTION OF SEED

Cell lines exhibiting satisfactory levels of resistance by virtue of having an altered herbicide site of action are put through a plant regeneration protocol to obtain mature plants and seeds expressing the resistance trait. The plant regeneration protocol allows the development of somatic embryos and the subsequent growth of roots and shoots. To determine that the herbicide resistance trait is expressed in differentiated organs of the plant and not solely in undifferentiated cell culture, early plant regeneration steps are carried out in the presence of herbicide levels that will normally inhibit shoot and root formation and growth.

Mature plants are then obtained from cell lines that are known to express the trait. If possible, the regenerated plants are self pollinated. Otherwise pollen obtained from the regenerated plants is crossed to seed grown plants of agronomically important inbred lines. Conversely, pollen from plants of these inbred lines is used to pollinate regenerated plants. The genetics of the trait is then characterized by evaluating the segregation of the trait in first and later generation progeny. The heritability and expression in plants of traits selected in tissue culture are of particular importance if the traits are going to be commercially useful.

5.5. DEVELOPMENT OF HERBICIDE RESISTANT COMMERCIAL HYBRID SEED

Seed from plants regenerated from tissue culture is grown in the field and self-pollinated to generate true breeding plants. The progeny from these plants become true breeding lines which are evaluated for herbicide resistance in the field under a range of environmental conditions. Herbicide resistance must be sufficient to protect the corn at maximum labeled rate under field conditions which cause the herbicide to be most active. Appropriate herbicide concentrations and methods of application are those which have been developed for the herbicide in question.

The commercial value of herbicide resistant corn is greatest if many different hybrid combinations with resistance are available for sale. The farmer typically grows more than one kind of hybrid based on such differences as maturity, standability or other agronomic traits. Additionally, hybrids adapted to one part of the corn belt are not adapted to another part because of differences in such traits as maturity, disease and insect resistance. Because of this, it is necessary to breed herbicide resistance into a large number of parental lines so that many hybrid combinations can be produced.

Adding herbicide resistance to agronomically elite lines is most efficiently accomplished if the genetic control of herbicide resistance is understood. This requires crossing resistant and sensitive plants and studying the pattern of inheritance in segregating generations to ascertain whether the trait is expressed as dominant or recessive, the number of genes involved, and any possible interaction between genes if more than one are required for expression. This genetic analysis can be part of the initial efforts to convert agronomically elite, yet sensitive, lines to resistant lines.

A conversion process (backcrossing) is carried out by crossing the original resistant line by sensitive elite lines and crossing the progeny back to the sensitive parent. The progeny from this cross will segregate such that some plants carry the resistance gene (S) whereas some do not. Plants carrying the resistance gene (S) will be crossed again to the sensitive parent resulting in progeny which segregate for resistance and sensitivity once more. This is repeated until the original sensitive parent has been converted to a resistant line, yet possesses all other important attributes as originally found in the sensitive parent. A separate backcrossing program is implemented for every sensitive elite line that is to be converted to an herbicide resistant line.

Subsequent to the backcrossing, the new resistant lines and the appropriate combinations of lines which make good commercial hybrids are evaluated for herbicide resistance, as well as a battery of important agronomic traits. Resistant lines and hybrids are produced which are true to type of the original sensitive lines and hybrids. This requires evaluation under a range of environmental conditions where the lines or hybrids will generally be grown commercially. Parental lines of hybrids that perform satisfactorily are increased and used for hybrid production using standard hybrid seed corn production practices.

5.6. ALTERNATE METHODS OF OBTAINING HERBICIDE RESISTANT MUTANTS

Generally, any alteration or replacement or elevation of AHAS which leads to herbicide resistance in tissue culture, seed and regenerated plants may be utilized in this embodiment of the present invention. AHAS may be altered or replaced or elevated in any plant species; of especially great importance are the agronomic and horticulture crops in which herbicides are utilized. Such plants include, for example, monocotyledonous plants and cereal crops such as maize, rice, wheat, barley, sorghum, oats, rye, millet and the like. The alteration of AHAS may be accomplished by any of a variety of means, including but not limited to the following methods: (1) spontaneous variation and direct mutant selection in tissue cultures; (2) direct or indirect mutagenesis procedures on tissue cultures of all types, seeds and plants; and (3) isolation of genes, manipulation, modification, or synthesis in whole or part of genes using molecular biology, chemical technologies, and state-of-the-art procedures and reintroduction of herbicide resistance genes into plants.

Additionally, any type of AHAS modification which leads to a change in resistance to, or tolerance of, chemical compounds applied to plants may be utilized. These changes may include alterations in enzyme structure and changes in enzyme expression and/or function. Chemical compounds include not only those which may be synthesized by techniques of organic chemistry, but also naturally occurring compounds which may affect AHAS activity in the plant, such as leucine and valine. Herbicide resistance may also be accomplished by replacement or supplementation (i.e., gene therapy or the addition of extra genes), by any means, of an endogenous AHAS with any other AHAS from another source, including but not limited to prokaryotic or eukaryotic organisms or by a total or partial chemical synthesis of a gene that catalyzes the same reactions as AHAS.

Genes encoding AHAS are common to the aspartate and branched chain amino acid pathways in plants and microorganisms (Umbarger, 1978, Ann. Rev. Biochem, 47: 533–606). AHAS catalyzes the first step in the synthesis of the amino acids leucine, valine and isoleucine. AHAS activity is regulated in vivo by various end products or combination of end products of the biosynthetic pathway. AHAS genes with a variety of regulatory characteristics are available from microorganisms including, but not limited to, *Escherichia coli*, yeast and Neurospora. These might include AHAS genes which are naturally resistant to the imidazolinone herbicides. For example, the isozymes of AHAS (I, II and III) present in the bacterium *E. coli* are insensitive to millimolar concentrations of AC 243,997 when assayed in vitro. Resistance of *E. coli* to AC 243,997 therefore appears to be the result of an insensitive site of action as opposed to being a result of metabolism of the herbicide. Resistance in other organisms is likely to be of the same nature, providing a variety of sources of a gene encoding an herbicide resistant AHAS. The genes encoding all three *E. coli* isozymes have been cloned and sequenced. Selection for imidazolinone resistant mutant AHAS genes in microorganisms or plants including plant tissue cultures would provide a diverse source of genes which, when transferred to plants, produce herbicide resistant plants.

To introduce isolated genes or groups of genes into the genome of plant cells an efficient host gene vector system is necessary. The foreign genes should be expressed in the transformed plant cells and stably transmitted (somatically and sexually) to the next generation of cells produced. The vector should be capable of introducing, maintaining and expressing a gene in plant cells, from a variety of sources, including but not limited to plants, animals, bacteria, fungi or viruses. Additionally it should be possible to introduce the vector into a wide variety of plants. The location of the new gene in the plant genome may be important in determining effective gene expression of the genetically engineered plant. In addition, to be effective, the new gene must be passed on to progeny by normal breeding.

Directed genetic modification and expression of foreign genes in dicotyledonous (broad-leafed) plants such as tobacco, potato and alfalfa has been shown to be possible using the T-DNA of the tumor-inducing (Ti) plasmid of *Agrobacterium tumefaciens*. Using recombinant DNA techniques and bacterial genetics, any foreign piece of DNA can be inserted into T-DNA in Agrobacterium. Following infection by the bacterium or Ti plasmid, the foreign DNA is inserted into the host plant chromosomes, thus producing a genetically engineered cell and eventually a genetically engineered plant. A second approach is to introduce root-inducing (Ri) plasmids as the gene vectors. While Agrobacterium appear to attack only dicots, many important crop plants (corn, wheat, rice, barley, oats, sorghum, millet and rye) are monocots and are not known to be susceptible to transformation by Agrobacterium. The Ti plasmid, however, may be manipulated in the future to act as a vector for monocot plants. Additionally, using the Ti plasmid as a model system it may be possible to artificially construct gene vectors for monocot plants.

Ti plasmids or other plasmids might also be introduced into monocots by artificial methods such as microinjection, or fusion between monocot protoplasts and bacterial spheroplasts containing the T-region which can then be integrated into the plant nuclear DNA.

Genetic engineering of plants may be accomplished by introducing the desired DNA containing functional genes encoding herbicide insensitive AHAS enzymes into plant tissues or cells using DNA molecules of a variety of forms and origins including but not limited to: plant pathogens such as DNA viruses like Cauliflower Mosaic virus (CaMV) or geminiviruses, RNA viruses, and viroids; DNA molecules derived from unstable plant genome components like extra-chromosomal DNA elements in organelles (e.g., chloroplasts or mitochondria), or nuclearly encoded controlling elements; DNA molecules from stable plant genome components (e.g., origins of replication and other DNA sequences which allow introduced DNA to integrate into the organellar or nuclear genomes and to replicate normally, to segregate normally during cell division and sexual reproduction of the plant and to be inherited in succeeding generations of plants).

The Cauliflower Mosaic virus (CaMV) has a gene the function of which is to prevent certain insects from destroying the virus. The remaining parts of the gene are redundant and can be replaced with a gene(s) which is useful to the plant breeder. The geminiviruses (or twin viruses) which are composed of two stands of DNA wrapped up in twin capsules of proteins can be used to transfer foreign genes into monocot plants. Transposons may also be used to carry foreign genes into plant DNA.

DNA containing AHAS genes may be delivered into the plant cells or tissues directly by infectious plasmids, such as Ti, viruses or microorganisms like *A. tumefaciens*, the use of liposomes, microinjection by mechanical or laser beam methods, by whole chromosome fragments, and by direct spraying of an infectious plant virus on crops.

Herbicide resistant plants can be developed using any of the means described supra and also other means including, but not limited to, conventional genetic and plant breeding procedures, whole plant genetic methods and somatic hybridization by protoplast fusion.

6. EXAMPLE

According to one particular embodiment of the present invention, the mechanism of action of the imidazolinone herbicides and the primary site of action of herbicidal activity was determined to be the enzyme, acetohydroxyacid sythase (AHAS). Maize tissue cultures resistant to an imidazolinone herbicide were selected and plants which were resistant to the herbicide were regenerated from these cultures. An altered AHAS enzyme was identified in herbicide resistant cultures. A detailed description of the invention is presented in the subsections below.

6.1. HERBICIDE SITE OF ACTION

Elucidation of the biochemical mechanism of action of the imidazolinone family of herbicides was carried out using the herbicidal compound AC 243,997 [2-(5-isopropyl-5-methyl-4-oxo-2-imidazolin-2-yl) nicotinic acid] hereinafter referred to as 997 (American Cyanamid Co., Princeton, N.J.). This compound is phytotoxic to most, if not all, higher plant species.

6.1.1. PLANT MATERIAL

Nonregenerable Black Mexican Sweet Corn cell suspension cultures (i.e., cell cultures which lack the ability to regenerate plants) were obtained from Dr. Burle Gengenbach, Department of Agronomy and Plant Genetics, University of Minnesota, St. Paul, Minn. Stock cell cultures were maintained in liquid Murashige and Skoog (MS) medium (Murashige and Skoog, 1962, Physiol. Plant 15: 473) containing 2 mg of 2,4-dichlorophenoxyacetic acid (2,4-D) per liter, and subcultured weekly by diluting to 1/10 the original volume with fresh medium. Cultures were grown in the dark at 26° C. in 500 ml flasks containing 125 ml media.

6.1.2. GROWTH INHIBITORY EFFECTS OF 997

Homogeneous, undifferentiated plant cell cultures (i.e., cell suspension cultures) provide a convenient system for studying herbicide mechanism of action at the biochemical level. An initial comparison of growth inhibitory effects of 997 on maize cell suspension cultures and maize seedlings derived from immature embryos was made. Growth inhibitory studies indicated that maize cell suspension cultures and maize seedlings responded in a similar way to 997, therefore maize cell suspension cultures were used as a model system in all studies of the biochemistry of herbicide action in the present embodiment of this invention.

Growth inhibition studies were carried out in 125 ml flasks containing 30 ml of test media. 997 was filter sterilized and added to cooling media following autoclaving. Test media were innoculated with cells to give a settled cell volume (15 minutes without centrifugation) of 0.2 ml per 10 ml of suspension. After either six or seven days growth settled cell volumes were again quantitated.

The herbicidal effects of 997 on maize seedlings were determined by evaluating germination and seedling growth from excised, mature maize embryos (Green, 1974, Crop Sci. 14: 54–58). Seeds were sterilized for 10 minutes in 0.5% hypochlorite and then imbibed for 24 hours in sterile, distilled water. Mature embryos were aseptically excised and plated on solid MS media (9% agar) containing various concentrations of 997 and no 2,4-D. Embryos were placed with their shoot axis away from the media. Shoot growth was quantitated after seven days.

Growth of both seedlings and suspension cultures was 50% inhibited at extremely low concentrations of herbicide, i.e., 1 to $3 \times 10^{-8}$ M in the media. Six maize inbred lines with different backgrounds, A188, A632 (Minnesota Crop Improvement Assoc., St. Paul, Minn.); W117 (University of Wisconsin, Madison, Wis.); and Mol7 (Illinois Crop Improvement Assoc., Champaign, Ill.) were tested and found to have identical sensitivities to 997 within the experimental limits of the assay. The highly differentiated seedlings and the undifferentiated suspension cells both showed a high degree of sensitivity to the herbicide which suggested that plant development was not required for expression of sensitivity, and the suspension cells could be used for preliminary studies on determining the mechanism of action of the compound 997.

6.1.3. EFFECTS OF 997 ON PROTEIN SYNTHESIS

Experiments were conducted to determine whether growth inhibitory levels of 997 had inhibitory effects on cell protein synthesis.

Suspension culture cells were preincubated for 48 hours in the presence or absence of $1\times10^{-5}$ M 997 and then exposed for 12 hours to 75 !Ci of either $^{35}$S-methionine (1210 Ci/mmol, New England Nuclear, Boston, Mass.) or $^{3}$H-DL-leucine (55 Ci/mmol, ICN Pharmaceuticals Inc. —K and K Laboratories, Plainview, N.Y.) per 0.1 ml of cells at a cell density of 10% volume cells/volume suspension. Cells were then centrifuged 300×g, washed with cold MS culture media, and ground with a cold mortar and pestle in the presence of one volume of 6 M urea. The resulting extract was centrifuged at 12,800×g for 5 minutes. The pellet was then reextracted and, following centrifugation, the extracts were combined. Protein was precipitated by the addition of 10% w/v trichloroacetic acid (TCA). Protein was removed by centrifugation and resolubilized in 6 M urea. Incorporation of radiolabel into protein was determined by scintillation counting.

At a concentration of $1\times10^{-5}$ M, 997 was found to significantly inhibit protein synthesis as determined by quantitating incorporation of radiolabeled amino acids into TCA-precipitable cell components. In experiments with cells at different post-subculture intervals, protein synthesis inhibition ranged from 50% to 77% on a cell fresh weight basis.

For determination of whether herbicide effects on protein synthesis were nonspecific, proteins were separated electrophoretically in one dimension on SDS (sodium dodecyl sulfate) 10% polyacrylamide slab gels (Laemmli, 1970, Nature 227: 680) and incorporation of radiolabel visualized by fluorography (data not shown). Cell volumes of 0.4 ml were exposed to $^{35}$S-methionine in the presence or absence of $1\times10^{-6}$ M herbicide as described supra, ground with mortar and pestle, and then extracted with 0.75 ml SDS sample buffer. The extracts were clarified by centrifugation and 20 !l or 4 !l samples loaded directly in the gels. The inhibition appeared to be nonspecific in nature. All major 6 M urea soluble intracellular protein components showed decreased levels of radiolabel.

6.1.4. DETERMINATION OF THE MECHANISM OF PROTEIN SYNTHESIS INHIBITION AND ITS RELATIONSHIP TO GROWTH INHIBITION

The effect of 997 on pool sizes of free amino acids was analyzed to determine if alterations in amino acid metabolism were associated with the changes in protein synthesis (see Table 1).

TABLE 1

Free Amino Acid Levels in Presence
and Absence of 1 × $10^{-5}$ M 997
(nmol per g fresh weight tissue)
Corn in Suspension Cultures

| Amino Acid | Control | 997 Treatment | |
|---|---|---|---|
| | | 3.5 hr. | 48 hr. |
| arg | 52 | 60[a] | 55 |
| trp | 22 | 30[a] | 30 |
| lys | 150 | 212 | 240 |
| his | 146 | 184 | 310 |
| phe | 124 | 151 | 195 |
| tyr | 96 | 112 | 130 |
| leu | 196 | 120 | 16 |
| ile | 121 | 120 | 38 |
| met | 51 | 100 | 405 |
| val | 397 | 355 | 48 |
| cystine[b] | 18 | 103 | 435 |
| ala | 336 | 600[a] | 455 |
| gly | 76 | 98 | 60 |
| glu | 235 | 360 | 175 |
| ser | 378 | 540 | 1160 |
| thr | 69 | 89 | N.D. |
| asp | 193 | 175 | 100 |

[a]Estimated
[b]Oxidized cysteine
N.D. = not done

Suspension culture cells were treated for 3.5 hours or 48 hours with $1\times10^{-5}$ M 997. Cells were removed from suspension by filtration and 1 gram fresh weight quantities were ground with sand with a mortar and pestle in 1 ml 5% TCA. Four ml of 5% TCA were added and the extract centrifuged at 10,000×g for 10 minutes. The pellet was reextracted and the supernatants combined and subjected to cation exchange chromatography. The samples were applied to Bond Elut SCX columns (Analytichem International Inc., Harbor City, Calif.) which had been equilibrated with 5% TCA. Following sample application, the columns were washed with 5 ml distilled, deionized water, and the amino acids were eluted with 2 ml aliquots of 5% v/v triethylamine. The aliquots were combined (6 ml), lyophilized, and subjected to amino acid analysis with a Kontron Liquemat III amino acid analyzer (Hesber, Middlesex TW5 OQU, England).

997 had a differential effect on the free amino acid levels in corn tissue growing in culture. The total free amino acids levels in Black Mexican Sweet Corn tissue treated with 997 increased over control cultures (Table 1). The biosynthetically related amino acids, serine, methionine, and cysteine, underwent the greatest increases during herbicide exposure (3, 8, and 24 fold, respectively, over a period of 48 hours). However, the biosynthetically related amino acids, leucine, valine, and isoleucine, decreased after herbicide treatment. After 48 hours of herbicide exposure, the levels of these amino acids decreased to 8, 12 and 31%, respectively, of the levels seen in untreated cell cultures.

Cells were tested to determine whether the herbicide induced inhibition of growth was the result of the decreased availability of the three branched chain amino acids. Cells were exposed to toxic levels of 997 ($1\times10^{-6}$ M) in media either supplemented with 1 mM concentrations of leucine, valine, and isoleucine or with no supplementation. Culture growth rates in the absence of amino acid supplementation and in the presence of $1\times10^{-6}$ M 997 were reduced to 16% that of herbicide free cultures. Supplementation with the branched chain amino acids resulted in growth rates averaging 91% that of control cultures, demonstrating an almost complete alleviation of herbicide induced growth inhibition.

Experiments were conducted to determine the optimum supplementation levels of each of the three amino acids to obtain maximum herbicide protection and for gaining insight into the site of action of the compound. The most effective combination of concentrations employed was 1 mM of each of the three amino acids. One mM each of leucine and valine appeared to be the most effective pairwise combination, and valine was most effective as a lone supplement (see Table 2).

TABLE 2

Reversal of 997 Inhibition of
Cell Suspension Culture Growth by
Leucine, Valine and Isoleucine

| | 1,1,1 | 1,1,.3 | 1,1,.1 | 1,.3,1 | 1,.3,.3 | 1,.3,.1 |
|---|---|---|---|---|---|---|
| (−) | 2.00 | 2.20 | 1.75 | 2.03 | 2.23 | 1.88 |
| (+) | 1.88 | 1.55 | .93 | 1.45 | 1.40 | .98 |
| | 1,.1,1 | 1,.1,.3 | 1,.1,.1 | .3,1,1 | .3,1,.3 | .3,1,.1 |
| (−) | 2.13 | 2.18 | 2.20 | 2.25 | 2.30 | 2.10 |
| (+) | 1.28 | 1.38 | 1.03 | 1.30 | 1.30 | 1.08 |
| | .3,.3,1 | .3,.3,.3 | .3,.3,.1 | .3,.1,1 | .3,.1,.3 | .3,.1,.1 |
| (−) | 2.20 | 2.33 | 2.33 | 2.25 | 2.25 | 2.25 |
| (+) | 1.08 | 1.18 | .95 | .80 | .95 | .70 |
| | .1,1,1 | .1,1,.3 | .1,1,.1 | .1,.3,1 | .1,.3,.3 | .1,.3,.1 |
| (−) | 2.20 | 2.20 | 2.05 | 2.38 | 2.25 | 2.20 |
| (+) | .60 | .68 | .83 | .80 | .90 | .75 |
| | .1,.1,1 | .1,.1,.3 | .1,.1,.1 | 0.3 val | 0.3 leu | 0.3 ile |
| (−) | 2.38 | 2.45 | 2.30 | 2.00 | 2.00 | 2.35 |
| (+) | .58 | .68 | .70 | .48 | .29 | .33 |

No Supplementation (4 replicates)

(−) 2.36
(+) 0.30

[1]Flasks were inoculated with 0.18 ml of cells per 10 ml media. Following growth for six days, the volume of cells per 10 ml media was quantitated. Numbers separated with commas refer to the mM concentrations of valine, leucine and isoleucine, respectively. (+) refers to the presence of $1 \times 10^{-6}$ M 997 and (−) to its absence. The values are the average of two replicates.

These results indicated that 997 induced growth inhibition and protein synthesis inhibition is a result of a decreased availability of the amino acids leucine, valine, and isoleucine. Additionally, the results implied that a major site of 997 action is associated with the leucine, valine, isoleucine biosynthetic pathway. It was further found that media supplementation with these three amino acids could reverse the growth inhibitory effects of 997 ranging in concentration from $1 \times 10^{-8}$ to $1 \times 10^{-3}$ M, indicating that this metabolic pathway contained the only significant site of action. (See FIG. 1.) Full reversal could not be obtained because of a toxic effect of the amino acids at high concentration.

Media supplementation with 1 mM each of leucine, isoleucine, and valine also reversed the growth inhibitory effects of two additional members of the imidazolinone family of chemicals structurally related to 997 (AC 252,214 [2-(5-isopropyl-5-methyl-4-oxo-2-imidazolin-2-yl)3-quinolinecarboxylic acid, hereinafter referred to as 214] and AC 263,499 [5-ethyl,2-(5-isopropyl-5-methyl-4-oxo-2-imidazolin-2-yl)nicotinic acid, hereinafter referred to as 499] (American Cyanamid Co., Princeton, N.J.) on cell suspension cultures. The results demonstrated that the observations made are not unique to 997 and indicated that a whole family of chemicals share the same mechanism and site of action.

6.1.5. IDENTIFICATION OF THE SITE OF ACTION OF THE IMIDAZOLINONE HERBICIDES

Herbicide structural information and herbicide toxicity reversal studies with the branched chain amino acids indicated acetohydroxyacid synthase to be the herbicide site of action.

Figure 2:
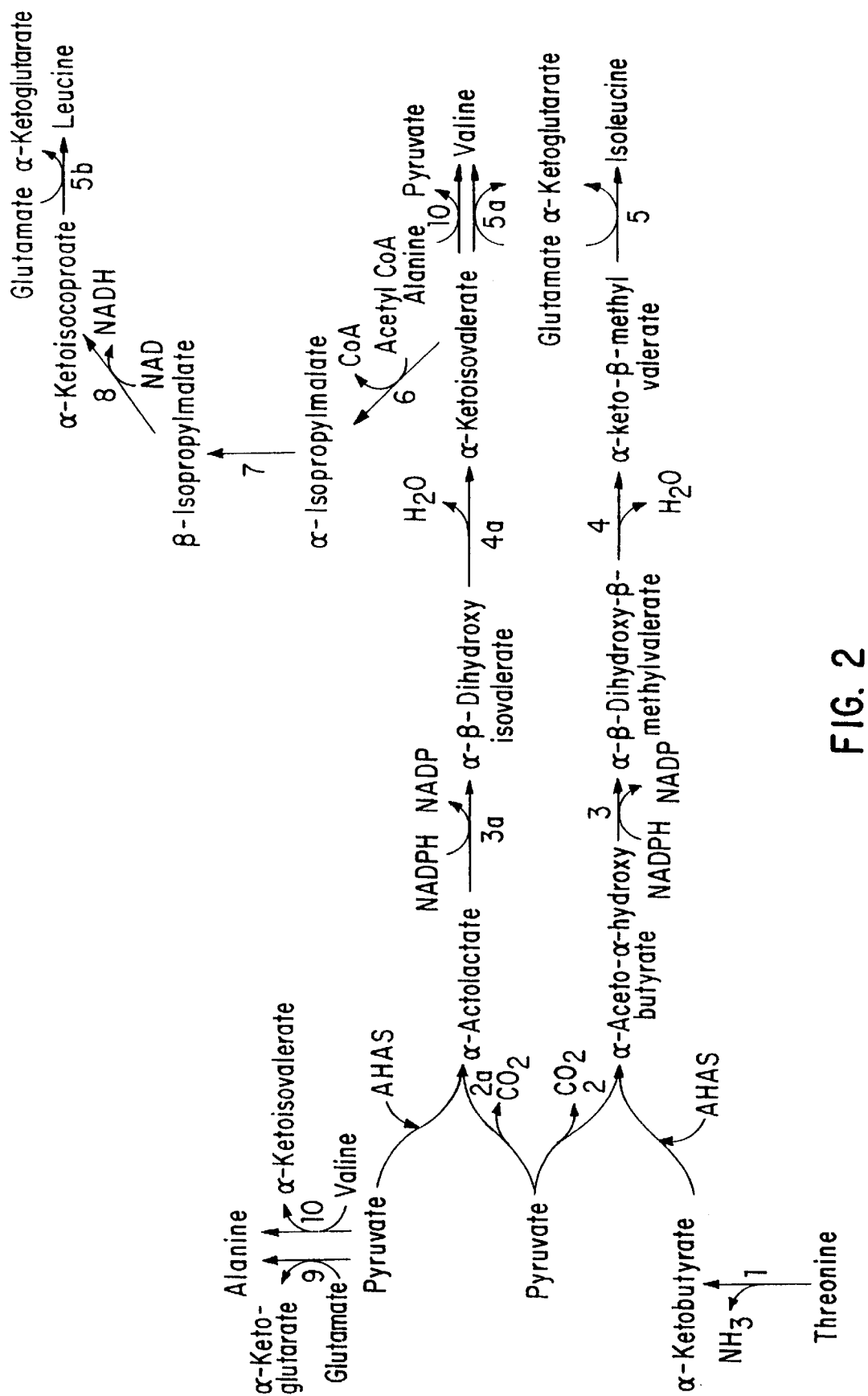
FIG. 2 shows the biosynthetic pathway for production of leucine, valine and isoleucine in plants.

The primary site of action of AC 243,997 probably resides at some reaction in the biosynthesis of leucine and valine from pyruvate and isoleucine from alpha-ketobutyric acid. (See FIG. 2.) Four enzymes in this pathway are shared in the synthesis of each of the three amino acids. Since media supplementation with all three amino acids is required for maximum alleviation of herbicide activity, these four enzymes are the most likely sites for herbicide interaction. The enzyme catalyzing the first reaction in the pathway from pyruvate is acetohydroxyacid synthase (AHAS). The following paragraphs describe studies which showed that the imidazolinones affect the activity of AHAS in vitro.

Assays were conducted as a modification of the procedure of Smith et al. (1979, Molec. Gen. Genet. 169: 299–314). Plant cell culture material was ground with sand in a cold mortar and pestle in an equal quantity (w/v) of cell disruption media containing 0.05 M potassium phosphate (pH 7.0), 0.1 mM $MgSO_4$, and 0.5 mM dithiothreitol. The preparation was centrifuged at 11,000×g for 20 minutes and the supernatant assayed for AHAS activity. Assays were conducted in 1 ml volumes containing 0.05 M potassium phosphate (pH 8.0), 40 mM pyruvate, 5 mM $MgCl_2$, 0.1 mM thiamine pyrophosphate, 0.2 ml cell extract, and various concentrations of the herbicide of interest. The reaction mixtures were incubated at 30° C. for 75 minutes and the reaction terminated with the addition of 0.1 ml of 50% (v/v) $H_2SO_4$. Following further incubation at 40° C. for 20 minutes, the acetoin formed from acetolactate by acidification was quantitated using the method of Westerfield (1945, J. Biol. Chem. 161: 495). To 0.2 ml of reaction mixture, 0.8 ml of water, 0.5 ml of 0.5% (w/v) creatine, and 0.5 ml of 5% (w/v) naphthol in 10% (w/v) NaOH was added. After mixing, solutions were incubated at room temperature for one hour. The development of pink color was quantitated by measuring light absorbance at 530 nm.

AHAS activity from maize cell cultures was found to be significantly inhibited by 997. Enzyme activity was reduced 50% by $8 \times 10^{-6}$ M 997. AC 252,214 and AC 263,499 also inhibited the enzyme activity. This data strongly indicated that AHAS was the primary site of phytotoxic activity of the imidazolinone family of herbicides.

Selection and characterization of a mutant with an altered AHAS that conferred herbicide resistance at the cellular level are described in the following subsections.

6.2. CHARACTERIZATION OF THE EFFECTS OF THE IMIDAZOLINONE HERBICIDES AND STRATEGY FOR SELECTION OF HERBICIDE RESISTANT MAIZE CELLS

6.2.1. INITIATION AND MAINTENANCE OF MAIZE CELL CULTURES WHICH RETAIN PLANT REGENERATION CAPACITY

Friable, embryogenic maize callus cultures were initiated from hybrid immature embryos produced by pollination of inbred line A188 plants (University of Minnesota, Crop Improvement Association) with pollen of inbred line B73 plants (Iowa State University). Ears were harvested when embryos had reached a length of 1.5 to 2.0 mm. The whole ear was surface sterilized in 50 v/v commercial bleach (2.63% w/v sodium hypochlorite) for 20 minutes at room temperature. The ears were then washed with sterile distilled, deionized water. Immature embryos were aseptically isolated and placed on nutrient agar initiation/ maintenance media with the root/shoot axis exposed to the media. Initiation/maintenance media consisted of N6 basal media (Chih-ching in Proceedings of Symposium on Plant Tissue Culture, May 25–30, 1978, Science Press, Peking, pp. 43–50) with 2% (w/v) sucrose, 1.5 mg per liter-2,4-D, 6 mM proline, and 0.9% (w/v) agar.

The immature embryos were incubated at 26° C. under dim light. Cell proliferations from the scutellum of the immature embryos were evaluated for friable consistency and the presence of well defined somatic embryos. Tissue with this morphology was transferred to fresh media 10 to 14 days after the initial plating of the immature embryos. The tissue was then subcultured on a routine basis every 12 to 16 days. Sixty to eighty mg quantities of tissue were removed from pieces of tissue that had reached a size of approximately one gram and transferred to fresh media. Subculturing always involved careful visual monitoring to be sure that only tissue of the correct morphology was maintained. The presence of the somatic embryos ensured that the cultures would give rise to plants under the proper conditions.

6.2.2. EFFECTS OF 997 ON FREE AMINO ACID LEVELS IN SUSPENSION CULTURES OF CELL LINE USED FOR SELECTION

The embryogenic cell line used in the selection for herbicide resistant cells (see Section 6.2.1) was different from the cell line used in the characterization of the site of action of 997 described in Section 6.1. Consequently, the effects of 997 on pool sizes of free amino acids in the cell line used in the selection procedure was also studied. The protocol described in Section 6.1.4 was followed for these studies. See Table 3.

TABLE 3

| Free Amino Acid Levels in Presence-(B) and Absence (A) of $1 \times 10^{-5}$ M 997 in Corn Suspension Cultures | | | |
| --- | --- | --- | --- |
| Amino acids | A Control | B AC243,997 treatment | B/A |
| (n mol per g fresh wt tissue)[1] | | | |
| ala | 2250 ± 50 | 5750 ± 1100 | 2.6 |
| arg | 50 ± 30 | 70 ± 60 | 1.4 |
| asp | 2550 ± 950 | 5700 ± 650 | 2.2 |
| glu | 2250 ± 1350 | 8550 ± 210 | 3.8 |
| gly | 240 ± 80 | 3130 ± 230 | 13.0 |
| ile | 90 ± 10 | 220 ± 10 | 2.4 |
| leu | 230 ± 10 | 120 ± 10 | 0.52 |
| lys | 130 ± 30 | 230 ± 140 | 1.8 |
| met | 50 ± 10 | 190 ± 80 | 3.8 |
| phe | 120 ± 10 | 790 ± 90 | 6.6 |
| ser | 2300 ± 500 | 20000 ± 2000 | 8.7 |
| thr | 460 ± 100 | 2960 ± 270 | 6.4 |
| tyr | 200 ± 30 | 410 ± 80 | 2.1 |
| val | 510 ± 50 | 140 ± 10 | 0.27 |

[1]Averages and standard deviations of three replicates. Trp, pro, cys, gln, asn and his not quantitated.

997 also exhibited a differential effect on the free amino acid levels in suspension cultures of the maize line used in the selection, but in somewhat different fashion from the nonregenerable cell line described in Section 6.1. As shown in Table 3, the biosynthetically related amino acids, leucine and valine, decreased after herbicide treatment.

This data, along with the data presented in Section 6.1, indicated that 997 exerted its herbicidal effect by decreasing the availability of the amino acids leucine and valine.

6.2.3. CALLUS CULTURE GROWTH INHIBITION BY IMIDAZOLINONE HERBICIDES

Since maize is generally grown in the field after soybean, it seemed reasonable to carry out selections for maize resistance to 214 (a soybean herbicide) rather than 997 (a total vegetative compound). Therefore the effects of 214 were determined on callus growth. Quantities of tissue averaging 90 mg in size were transferred to nutrient agar maintenance media containing concentrations of 214 ranging from 0.003 to 3 mg per liter. Eight tissue pieces were placed on each plate with three plates per herbicide concentration. After 14 days growth, the tissue was weighed again. Inhibition of growth rate was found to be half maximal in the 0.1 to 0.3 mg per liter range of concentration of 214. Cell death was not observed to occur over a 14 day period at any of the tested herbicide concentrations. However, culture morphology changes did occur at herbicide concentrations that gave more than half maximal inhibition of growth rate. Especially obvious was the loss of somatic embryo formation.

Growth inhibition studies carried out over periods of time greater than 14 days, in which tissue was grown either in the presence of herbicide on the same plates for more than 14 days or was transferred to fresh plates containing the same herbicide concentrations, showed half maximal growth inhibitory effects at smaller herbicide concentrations (3 to 10 fold). Therefore, the growth inhibitory effects of the herbicide increased with time as well as with increased quantities of herbicide in the media. This observation demonstrated that the herbicide was very persistent, i.e., it was probably not metabolized to any great extent and accumulated in the tissue.

6.2.4. REVERSIBLE EFFECTS OF 214

To determine whether the effects of 214 were reversible, Black Mexican Sweet Corn cells growing in liquid suspension culture were exposed to 0.03 mg per liter 214 for various periods of time up to 72 hours. Growth was completely inhibited. The cells were then washed with herbicide-free media and the growth rate evaluated again in the absence of herbicide. Cells were found to rapidly return to an uninhibited growth rate. During the herbicide exposure, cells did not divide but remained viable and resumed divisions once the herbicide was removed. The reversible nature of the herbicide induced growth inhibition indicated that continuous herbicide exposure should be used in the selection procedure as opposed to intermittent exposures of a given duration.

6.3. SELECTION AND CHARACTERIZATION OF AN HERBICIDE RESISTANT CELL LINE

The selection protocol used to identify and isolate herbicide resistant cells was formulated to take into account that: (1) the effects of the herbicides were reversible; (2) the effects of the herbicides increased over time; and (3) high herbicide concentrations adversely affected somatic embryo development and potentially plant regeneration capacity. Therefore, the procedure involved exposing tissue continuously to low herbicide concentrations over several subculture intervals and keeping careful records of the growth of all tissue in the selection. In this way the herbicide was allowed to take effect slowly with continuous selection pressure permitting herbicide tolerant cells to accumulate over time and yet not affect the potential for plant regeneration. This procedure allowed for the selection of cells with even small levels of herbicide tolerance (2 to 3 fold in herbicide concentration).

6.3.1. SELECTION OF AN HERBICIDE RESISTANT CELL LINE

Many selections were carried out utilizing the selection protocol described supra. The selection of one such herbicide resistant line that was identified and characterized is described below in detail.

Approximately thirteen grams of vigorously growing maize callus tissue was transferred to maintenance media in petri plates containing 0.03 mg per liter of herbicide 214. Thirty plates were prepared and 80–90 mg of tissue were plated in 5 areas on each plate. The herbicide level was chosen from growth inhibition studies to provide less than 20% to 40% growth inhibition during the first two weeks of herbicide exposure.

After 10 days the tissue had increased in mass over four fold. Eighty to 90 mg pieces of tissue showing vigorous growth rate and retention of embryogenic morphology (i.e., presence of somatic embryos) were subcultured on fresh media containing 0.03 mg per liter 214. Thirty plates containing an average of seven pieces of tissue per plate were prepared. Each piece of tissue was labeled and became the progenitor of a "line." A complete genealogy was maintained and recorded for future subcultures. Subsequent subculture intervals ranged from 15 to 30 days depending on overall growth of the callus tissue.

For each transfer all tissue showing growth and somatic embryo forming ability were placed on fresh media, and the number of uniform sized callus pieces within a given "line" was recorded. During the course of the selection process, the total number of lines decreased as the herbicide mediated growth inhibition became more intense. Many lines however, increased in size. At the end of the fifth selection cycle, the level of 214 was raised to 0.1 mg per liter to increase the selection pressure.

Between the fifth and sixth selection cycles, the amount of tissue in line XA17 began to increase significantly. The tissue showing the increased growth rate had a morphology different from the parent material from which the selection was initiated. Cells were smaller on the average and more cytoplasmically dense, giving the tissue a yellow hue. The tissue continued to grow rapidly over subsequent subculture intervals until the vast majority of the tissue in the selection was identified as line XA17. At the seventh subculture, tissue of line XA17 was removed from the selection for the purpose of characterization. This stock tissue was maintained and accumulated on maintenance media described supra in Section 6.2.1 containing 0.1 mg per liter 214.

6.3.2. CHARACTERIZATION OF MAIZE CELL LINE XA17

The resistant cell line was characterized to evaluate: (1) the magnitude of the resistance; (2) the chemical spectrum of the resistance; and (3) the biochemical basis for the resistance.

Initially, the maximum level of 214 in which line XA17 would grow stably was determined. Stock tissue which had been maintained in the presence of 0.1 mg per liter 214 was transferred to media containing 214 levels ranging up to 30 mg per liter. Tissue was maintained for several subculture intervals and the growth rate evaluated. Line XA17 tissue grew normally at a maximum level of 214 of 3.0 mg per liter as compared with a maximum of 0.01 mg per liter 214 for unselected tissue.

Two week growth inhibition studies were carried out (as described supra) with 214, 997, 499, 567 and chlorsulfuron. The levels of 214, 997, 499 and 567 giving a 50% growth inhibition were found to be 30 mg per liter for 214, and higher than 30 mg per liter for 997, 499 and 567 as compared with levels of 0.1 to 0.3 mg per liter for unselected tissue. The growth rate of line XA17 tissue was 50% inhibited by 10 mg per liter chlorsulfuron 2-chloro-N-[(4-methoxy-6-methyl-1,3,5-triazin-2-yl)aminocarbonyl] benzenesulfonamide, also known as chsorsulfuron, DPX 4189, E.I. DuPont de Nemours and Company, Wilmington, Del.) as compared with 0.01 mg per liter for unselected tissue. Although line XA17 was selected for resistance to 214, it expressed at least a three hundred fold enhancement of resistance (on a concentration basis) to the other compounds tested.

6.3.3. AHAS ACTIVITY OF MAIZE LINE XA17

Assays were conducted to determine if acetohydroxyacid synthase extracted from line XA17 tissue was altered with respect to herbicide sensitivity. Such a change would signify that an alteration of this enzyme conferred the herbicide resistance. Assays were conducted as described supra. AHAS activity of control tissue was 50% inhibited by 997, 214 and 499 in the concentration range of $1 \times 10^{-6}$ to $1 \times 10^{-5}$ M. AHAS activity of line XA17 tissue was 50% inhibited by 997, 214 and 499 in the $3 \times 10^{-3}$ to $3 \times 10^{-2}$ M range of herbicide concentration, indicating at least a 1000 fold change in herbicide sensitivity on a concentration basis. AHAS activity of control tissue was found to be 50% inhibited by $1 \times 10^{-8}$ M chlorsulfuron compared with a 50% inhibition of line XA17 AHAS at $3 \times 10^{-7}$ M.

The results demonstrate that AHAS is the site of action of the herbicides tested, and furthermore, resistance was conferred by an alteration of the site of action. Since line XA17 expresses resistance at the cellular level by virtue of having an altered site of action, the herbicide tolerance is likely to extend to many compounds that act at the same sites or other sites on AHAS, including all members of the imidazolinone and sulfonamide families of herbicides.

The imidazolinone and sulfonamide families of herbicides are structurally dissimilar. Although they both inhibit AHAS activity in plants, it is possible they are interacting with different sites on the enzyme. If they interact with different sites, then the alteration in XA17 AHAS which gave rise to imidazolinone resistance is apparently substantial enough to affect both sites. The AHAS alteration of XA17 tissue may also affect the binding of compounds other than the imidazolinones or sulfonamides which interact with the enzyme. Further, it may be possible to obtain other mutants with alterations of AHAS that possess a variety of selectivities for different herbicidal compounds that affect AHAS, e.g., a mutant that is tolerant only of the imidazolines and not of the sulfonamides.

Whether the above explanation of sites of action affected by the herbicides is correct or not, the fact remains that callus tissue and regenerated plants of line XA17 express substantial amounts of tolerance to members of both families of herbicides compared with other maize cell cultures or plants.

6.4. PLANT REGENERATION AND PRODUCTION OF SEED

6.4.1. PLANT REGENERATION PROTOCOL

Eighty to 90 mg quantities of maize callus tissue were transferred to embryo and shoot development (regeneration) media in petri plates. The media consisted of MS basal media supplemented with 0.1 mg per liter 2,4-D and $1 \times 10^{-7}$ M abscissic acid. 0.25% Gelrite (Kelco Co., San Diego, Calif.) was used as a solid support in place of agar. The tissue was incubated in the dark at 26° C. (approximately 300 footcandles, soft white fluorescent) on a cycle of 14 hours light, 10 hours dark. Developing plants reaching a size of 1–3 cm were then transferred to flasks or jars, containing MS media with no supplementation, for further development. When plants reached the two to three leaf stage, they were moved to pots containing vermiculite and exposed to light at 2600 footcandles. These plants were watered with 20% v/v MS media for one week and then with water until they grew stably. The plants were then transferred to soil for growth to maturity.

6.4.2. HERBICIDE INHIBITION OF PLANT REGENERATION

The effect of various concentrations of 214 on plant regeneration embryo and shoot development were evaluated. Unselected culture tissue was transferred to regeneration media containing various concentrations of 214 ranging from 0.01 to 0.3 mg per liter. The tissue was then put through the first three weeks of the plant regeneration protocol described supra. The culture was scored after this time for the production of well defined shoots.

Plant regeneration was 50% inhibited by 214 in the concentration range of 0.03 to 0.1 mg per liter based on the number of shoots formed. 0.3 mg per liter 214 completely inhibited somatic embryo development and shoot formation.

6.4.3. EXPRESSION OF HERBICIDE RESISTANCE IN PLANTS REGENERATED FROM LINE XA17 CALLUS TISSUE

Traits which are selected for and expressed in undifferentiated cell cultures are not necessarily expressed in the differentiated organs and tissues of a developing plant. Therefore, it was necessary to examine plants regenerated from line XA17 callus tissue in the presence of normally inhibitory concentrations of 214. Line XA17 tissue was transferred to regeneration media containing 0.1, 0.3, and 3.0 mg per liter 214. Normally developing plantlets were obtained at all three herbicide levels, demonstrating that herbicide resistance was expressed during plant development.

6.4.4. REGENERATION OF MATURE PLANTS AND PRODUCTION OF SEED

Mature plants were regenerated from line XA17 callus tissue that had either been removed from herbicide exposure for at least three subculture cycles or had been continuously exposed to 0.1, 0.3 or 3.0 mg per liter 214 on maintenance media. Plant regeneration frequency in all instances was approximately 1 plant per 100 g cell culture. Plants were grown to maturity, and the pollen obtained was used to fertilize plants of inbred line B73. Conversely, pollen from B73 plants was crossed to line XA17 regenerated plants. The seed obtained was found to germinate under normal planting conditions.

6.4.5. EXPRESSION OF HERBICIDE RESISTANCE IN PROGENY OF REGENERATED PLANTS

Seedling assays of progeny obtained from plants regenerated from cell line XA17 were performed as described below to determine whether the herbicide resistance selected in culture was inherited and expressed in plants following a sexual cycle.

An XA17 regenerated plant with a normal ear was pollinated with pollen obtained from a herbicide sensitive inbred B73 plant grown from seed. Seeds were obtained and harvested approximately forty days post pollination.

Seeds to be used as controls in the heritability assay were obtained from regenerated plants from an herbicide sensitive cell line of the same genetic background as line XA17. These regenerated plants were crossed with pollen obtained from a herbicide sensitive inbred B73 plant grown from seed. Seeds were harvested approximately forty days after pollination.

Twenty control seeds and ten XA17 seeds were surface sterilized with 2.6% sodium hypochlorite for twenty minutes and then washed with sterile distilled water. The seed was imbibed overnight in sterile water containing a small quantity of the fungicide, captan (N-trichloromethylthio-4-cyclohexene-1,2-dicarboximide). The mature embryos were then excised from the seed and plated scutellum side down on solid MS media without 2,4-D. Ten control seeds were plated on media containing no 214 and ten were plated in the presence of $6 \times 10^{-8}$ M 214 which had been incorporated into the medium after autoclaving but before gelling. All ten XA17 seeds were plated in the presence of $6 \times 10^{-8}$ M 214. Seedlings were evaluated seven days after plating.

Figure 3:
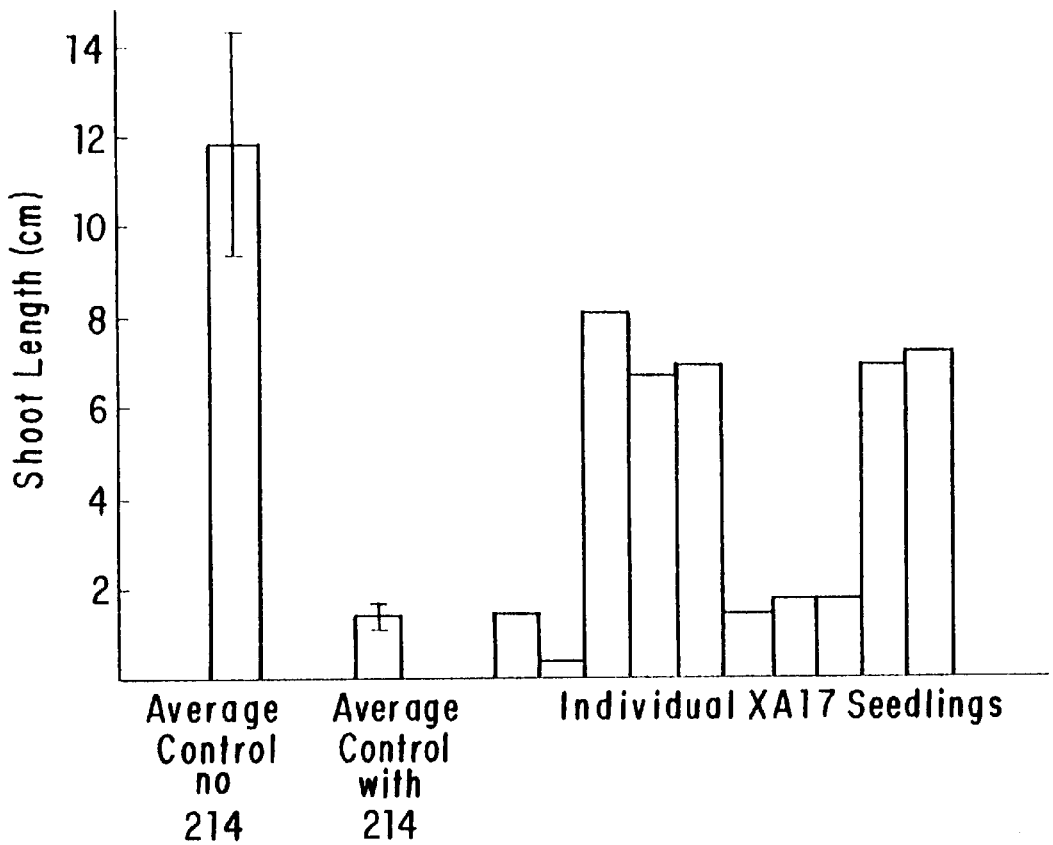
FIG. 3 shows the shoot length growth of seedlings grown in the presence or absence of AC 252,214.
Figure 4:
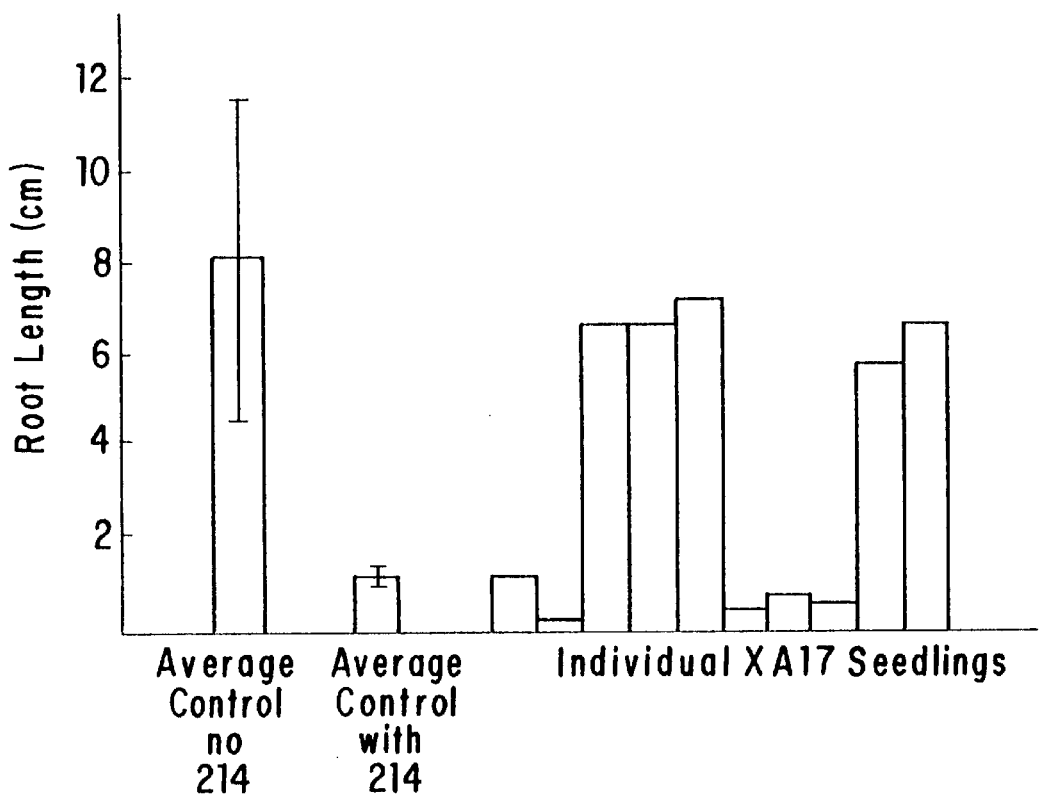
FIG. 4 shows the root length growth of seedlings grown in the prescence or absence of AC 252,214.

Control seedlings in the absence of 214 grew normally throughout the seven day period attaining an average shoot length of 11.8 cm (FIG. 3) and an average root length of 8.1 cm (FIG. 4). Growth inhibition of control seedlings in the presence of 214 was first observed on day three. No further growth took place in subsequent days. The average shoot length and root length attained were 1.5 and 1.1 cm, respectively.

Of the ten XA17 seedlings grown in the presence of 214, the growth of five seedlings was inhibited to the same degree as control seedlings grown in the presence of 214. Five XA17 seedlings showed resistance to growth inhibition of 214 (FIG. 3 and FIG. 4).

Root growth of the resistant seedlings was particularly striking. The roots penetrated the herbicide containing media and grew rapidly with substantial branching and attained lengths of 6–7 cm. Roots of sensitive seedlings grew little (0–1 cm) and remained on the surface of the media. The data indicate that the herbicide resistance trait which was selected in culture is inherited as a dominant gene (or genes) and that it provides a high level of resistance to 214 in plants. The level of 214 tolerance observed for these seedlings, which are heterozygous for the tolerance trait, is at least 5 fold on an herbicide concentration basis.

Resistant and sensitive seedlings were transferred to pots for growth to maturity. The trait is being crossed from these plants to agronomically important inbred lines for commercial development.

6.4.6. METHOD FOR OBTAINING UNIFORM HERBICIDE RESISTANT SEED

Seed from herbicide resistant regenerated plants obtained from crosses with herbicide sensitive plants segregate one resistant to one sensitive for the herbicide resistance trait. That is, half the seeds possess a single gene encoding resistance and half the seeds have no resistance. Seeds which uniformly express the trait and are heterozygous or homozygous with respect to the resistant acetohydroxyacid synthase gene may be obtained by performing the following crosses and assays.

Seed obtained from herbicide resistant regenerated plants which have be en crossed with se nsitive plants are planted, grown to sexual maturity, and self pollinated. Samples of seed harvested from the resulting ears are assayed for herbicide resistance using a seedling assay. Half the ears will have no resistant seed. The other half will have seed expressing the resistance trait with the trait segregating 1:2:1 (homozygous resistant: heterozygous resistant: homozygous sensitive), i.e., 75% of the seed carrying the resistance trait.

Seed from the ears possessing the resistance trait are then grown and self pollinated. Seed from the resulting ears are again assayed for resistance. Twenty-five percent of these ears will have seed that uniformly express herbicide resistance. These seed are homozygous for the resistance trait and come from homozygous plants.

Seed that are uniformly heterozygous for the resista once trait may be obtained by growing plants from the homozygous seed and using these plants as either male or female parents in crosses with plants lacking the resistance gene. Progeny from these crosses are uniformly herbicide resistant and heterozygous for the resistance gene.

6.4.7. HERBICIDE RESISTANCE OF PLANTS HOMOZYGOUS FOR THE RESISTANCE TRAIT

Figure 5:
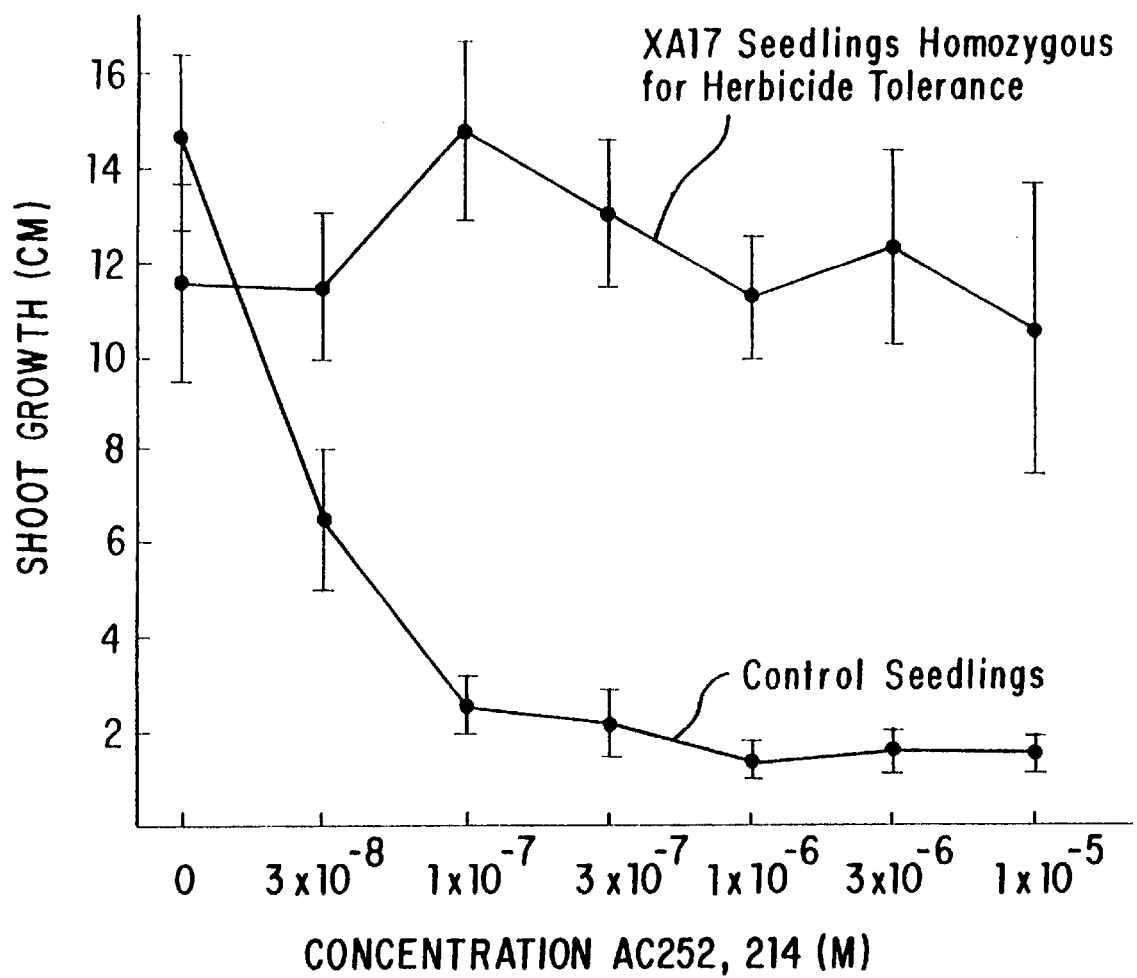
FIG. 5 shows the shoot length of herbicide tolerant and sensitive seedlings grown in the presence of a range of concentrations of AC 252,214.

XA17 seeds homozygous for the resistance trait were reobtained as described in Section 6.4.6. Seedling assays were conducted with this material to determine the magnitude of resistance to 214, 567 and chlorsulfuron. Assays were conducted as described in Section 6.4.5. Control seeds used were ones lacking the resistance trait but otherwise possessing a genetic background like that of the resistant seeds Shoot growth of control seedlings was found to be 50% inhibited by $3\times10^{-8}$ M 214, $1\times10^{-7}$ M 567, and $1\times10^{-8}$ M chlorsulfuron. Shoot growth of seedlings homozygous for the resistance trait was 50% inhibited by $1\times10^{-7}$ M chlorsulfuron and showed no inhibition by 214 (FIG. 5) or 567 at the highest concentration tested, $3\times10^{-6}$ M.

To summarize, XA17 seedlings homozygous for the herbicide resistance trait showed 10 fold resistance to chlorsulfuron, at least 30 fold resistance to 567, and at least 100 fold resistance to 214.

7. EXAMPLE
7.1. SELECTION OF ADDITIONAL HERBICIDE RESISTANT CELL LINES

The following sections briefly describe the selection and partial characterization of two additional imidazolinone resistant maize cell lines, QJ22 and UV18. Line QJ22 possesses a different pattern of resistance to the imidazolinone and sulfonamide herbicides as compared to lines XA17 and UV18.

7.1.1. SELECTION OF CELL LINE QJ22

Line QJ22 was selected from maize cell culture using the protocol described in detail for the selection of line XA17 (Section 6.3.1) with the following significant differences: (1) maize callus tissue was selected using the herbicide 499; and (2) the tissue used to initiate the selection was obtained from a previously selected cell line XA119. XA119 was identified in a selection for 214 tolerance and had been demonstrated to have an approximately three fold enhancement of tolerance to 214 at the cellular level.

The selection which resulted in the identification of line QJ22 was initiated at a 499 concentration of 0.1 mg per liter. The selection was maintained through two very long subculture intervals covering a 12 week period of time. Line QJ22 was identified after 12 weeks of selection as a rapidly growing sector of tissue with good tissue morphology. QJ22 tissue was increased over the following weeks in the presence of 0.1 mg per liter 499. After 8 weeks of accumulation, the cell line was characterized and plant regeneration effort initiated.

7.1.2. SELECTION OF CELL LINE UV18

Line UV18 was also selected from maize cell culture using the protocol described in detail for the selection of line XA17 with one important difference. The tissue used to initiate the selection was subjected to irradiation with ultraviolet light before being exposed to 214.

For the ultraviolet light exposure, tissue was spread in a thin layer (1–3 mm) on maintenance media in plastic petri dishes. These plates were then irradiated with UV light for periods of 0, 1, 2, 4, and 8 minutes in the absence of visible light. The ultraviolet light source was a Westinghouse model 782L-30 29W lamp (Westinghouse Electrical Corporation, Lamp Commercial Division, Bloomfield, N.J.) placed approximately seven inches from the tissue. The irradiated tissue was grown in the dark for two weeks. Surviving tissue was then transferred to maintenance media containing 0.1 mg per liter 214 to initiate selection for 214 resistance.

Line UV18 was identified from tissue which had obtained a 2 minute exposure to ultraviolet light. It could not be determined whether the alteration giving rise to 214 tolerance was a result of the ultraviolet radiation or a spontaneous variation that occurred during the selection process.

The UV18 cell line was first observed after 25 weeks of selection comprising 9 subculture intervals. The tissue in the selection procedure had been exposed to 0.1 mg per liter 214 for four subculture intervals followed by exposure to 0.3 mg per liter 214 for four subculture intervals. UV18 was identified during the ninth subculture as a rapidly growing sector of tissue with good morphology. The tissue grew as rapidly in the presence of 0.3 mg per liter 214 as did control tissue in the absence of herbicide.

The cell line was rapidly increased in the presence of 214 and characterized. Plants were regenerated in the presence of normally toxic levels of 214 (0.3 mg per liter) demonstrating the resistance trait was expressed in differentiated plant organs. Herbicide resistant plants regenerated from the UV18 cell culture are presently being grown to maturity.

7.1.3. CHARACTERIZATION OF LINES QJ22 AND UV18

The resistant callus tissues were characterized to determine the magnitude and spectrum of herbicide tolerance.

Callus tissue from lines QJ22 and UV18 was subjected to growth inhibition studies with a series of concentrations of the compounds 214, 997, 499 and chlorsulfuron. Callus tissue from line QJ22 was tested also with the compound 567. Table 4 describes the results of these studies. The numbers represent the fold increase in herbicide concentration that can be tolerated by each of the cell lines as compared to control tissue. The values were calculated based on the amount of herbicide that gave a 50% reduction in growth rate. In the instance where greater than 100 fold resistance is displayed, the tissue was completely tolerant of the highest concentration tested. UV18, in general, showed a tolerance of the herbicides similar to that of line XA17. QJ22 is significantly different from UV18 and XA17. QJ22, for example, showed a much smaller degree of tolerance of 214 and essentially no tolerance of 567 or chlorsulfuron was observed.

TABLE 4

| Selected Line | Callus Growth Fold Increase in Tolerance | | | | |
|---|---|---|---|---|---|
| | 997 | 214 | 499 | 567 | Chlorsulfuron |
| QJ22 | 30–50 | 5 | 30–50 | 0 | 0 |
| UV18 | 100 | 100 | 100 | | 300 |

7.1.4. HERBICIDE INHIBITION OF AHAS ACTIVITY OF LINES QJ22 AND UV18

Acetohydroxyacid synthase activity was extracted from cell lines UV18 and QJ22 and assayed as described in detail for cell line XA17, supra. AHAS activity from both selected lines was more tolerant of 997 over a 100 fold range of 997 concentrations ($3\times10^{-6}$ to $3\times10^{-4}$ M) than was AHAS activity from control cultures. Tolerant AHAS activity from line QJ22 was most clearly observed when the AHAS activity was extracted from QJ22 callus which had been growing in the presence of an imidazolinone herbicide. The results suggest that UV18 and QJ22, like XA17, are herbicide resistant by virtue of having an altered herbicide site of action. Additionally, other mechanisms may be involved in imparting herbicide resistance in these cell lines.

7.1.5. EXPRESSION OF HERBICIDE RESISTANCE IN PROGENY OF REGENERATED PLANTS OF LINE QJ22

Plants were regenerated from cell line QJ22 and seed obtained as described previously for XA17, supra. Seedling assays conducted on second and third generation progeny of the regenerated plants indicated that the resistance trait was inherited as a single dominant gene. Seeds which are uniformly homozygous for the resistance trait were obtained as described for XA17, supra. Their magnitude of resistance to 499, 567, and chlorsulfuron was determined with seedling assays. The seedlings were found to possess 30 fold tolerance of 499 as compared to control seedlings of appropriate genetic background. The seedlings showed no tolerance of 567 or chlorsulfuron.

The spectrum of tolerances of the various herbicides tested with QJ22 is clearly different than what was observed for XA17, strongly suggesting that more than one mutation providing resistance to the imidazolinones or sulfonamides may be obtained. The evidence also suggests that the different mutations are associated with different alterations of the herbicides' site of action, although other resistance mechanisms may also be involved in line QJ22 tolerance such as selective metabolism of the imidazolinones.

The different AHAS alterations may reflect different changes in a single gene encoding AHAS activity; changes in more than one gene which encode different subunits of a multimeric AHAS enzyme; or changes in more than one gene encoding separate AHAS isozymes. It is expected that other alterations of the site of action are possible providing other novel spectra of resistances to the herbicides, e.g., a mutant that possess broad sulfonamide tolerance but no imidazolinone tolerance. Such additional alterations of enzymes and plants containing them are also within the scope of this invention.

8. DEPOSIT OF CELL LINES AND SEEDS

The following cell lines described herein have been deposited with the American Type Culture Collection, Manassas Va., and have been assigned the following accession numbers:

| Cell Line | Accession Numbers |
| --- | --- |
| XA17 | 40100 |
| QJ22 | 40129 |
| UV18 | 40128 |

Seeds derived from plants grown from cell line XA17 and QJ22 as described herein have been deposited with In Vitro International, Inc., Ann Arbor, Mich. and have been assigned IVI accession No. 10011 and No. 10110, respectively.

These seed deposits have been transferred to the American Type Culture Collection (ATCC), 10801 University Boulevard, Manassas, Va. 20110-2209, where they are identified by ATCC No. 75134 (XA17) and ATCC No. 75135 (QJ22).

The present invention is not to be limited in scope by the cell lines or seeds deposited, since the deposited embodiments are intended as single illustrations of one aspect of the invention and any cell lines or seeds which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A monocotyledonous seed from which a plant can be grown, the growth of which plant is resistant to inhibition by a 2-(2-imidazolin-2-yl)pyridine herbicide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, and wherein the plant is of a species in which fertile plants can be regenerated from tissue culture.

2. A seed according to claim 1, wherein the 2-(2-imidazolin-2-yl)pyridine herbicide is AC 263,499.

3. A seed according to claim 1, wherein the 2-(2-imidazolin-2-yl)pyridine herbicide is AC 243,997.

4. A seed according to claim 1, 2 or 3, wherein the plant is a cereal.

5. A seed according to claim 1, 2 or 3, wherein the plant is selected from the group consisting of rice, wheat, barley, sorghum, oats, rye and millet.

6. A monocotyledonous seed from which a plant can be grown, the growth of which plant is resistant to inhibition by a 2-(2-imidazolin-2-yl)quinoline herbicide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, and wherein the plant is of a species in which fertile plants can be regenerated from tissue culture.

7. A seed according to claim 6, wherein the 2-(2-imidazolin-2-yl)quinoline herbicide is AC 252,214.

8. A seed according to claim 6 or 7, wherein the plant is a cereal.

9. A seed according to claim 6 or 7, wherein the plant is selected from the group consisting of rice, wheat, barley, sorghum, oats, rye and millet.

10. A monocotyledonous seed from which a plant can be grown, the growth of which plant is resistant to inhibition by an herbicidal sulfonamide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, and wherein the plant is of a species in which fertile plants can be regenerated from tissue culture.

11. A seed according to claim 10, wherein the herbicidal sulfonamide is 2-chloro-N[(4-methoxy-6-methyl-1,3,5-triazin-2-yl)aminocarbonyl] benzenesulfonamide.

12. A seed according to claim 10 or 11, wherein the plant is a cereal.

13. A seed according to claim 10 or 11, wherein the plant is selected from the group consisting of rice, wheat, barley, sorghum, oats, rye and millet.

14. A monocotyledonous seed from which a plant can be grown, the growth of which plant is resistant to inhibition by a 1,2,4-triazolo[1,5-a]pyrimidine-2-sulfonamide herbicide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, and wherein the plant is of a species in which fertile plants can be regenerated from tissue culture.

15. A seed according to claim 14, wherein the 1,2,4-triazolo[1,5-a]pyrimidine-2-sulfonamide herbicide is 5,7-dimethyl-N-(2,6-dichlorophenyl)-1,2,4-triazolo[1,5-a]pyrimidine-2-sulfonamide.

16. A seed according to claim 14 or 15, wherein the plant is a cereal.

17. A seed according to claim 14 or 15, wherein the plant is selected from the group consisting of rice, wheat, barley, sorghum, oats, rye and millet.

18. A monocotyledonous seed from which a plant can be grown, the growth of which plant is resistant to inhibition by a 2-(2-imidazolin-2-yl)pyridine herbicide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, wherein the growth of said plant is sensitive to inhibition by an herbicidal sulfonamide, or an herbicidal derivative thereof, at levels which normally inhibit the growth of that species of plant by inhibiting the activity of acetohydroxyacid synthase, and wherein the plant is of a species in which fertile plants can be regenerated from tissue culture.

19. A seed according to claim 18, wherein the 2-(2-imidazolin-2-yl)pyridine herbicide is AC 263,499.

20. A seed according to claim 18, wherein the 2-(2-imidazolin-2-yl)pyridine herbicide is AC 243,997.

21. A seed according to claim 18, 19 or 20, wherein the herbicidal sulfonamide is 2-chloro-N[(4-methoxy-6-methyl-1,3,5-triazin-2-yl)aminocarbonyl] benzenesulfonamide.

22. A seed according to claim 18, 19 or 20, wherein the plant is a cereal.

23. A seed according to claim 18, 19 or 20, wherein the plant is selected from the group consisting of rice, wheat, barley, sorghum, oats, rye and millet.

24. A monocotyledonous seed from which a plant can be grown, the growth of which plant is resistant to inhibition by a 2-(2-imidazolin-2-yl)pyridine herbicide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, wherein the growth of said plant is sensitive to inhibition by a 1,2,4-triazolo[1,5-a]pyrimidine-2-sulfonamide herbicide, or an herbicidal derivative thereof, at levels which normally inhibit the growth of that species of plant by inhibiting the activity of acetohydroxyacid synthase, and wherein the plant is of a species in which fertile plants can be regenerated from tissue culture.

25. A seed according to claim 24, wherein the 2-(2-imidazolin-2-yl)pyridine herbicide is AC 263,499.

26. A seed according to claim 24, wherein the 2-(2-imidazolin-2-yl)pyridine herbicide is AC 243,997.

27. A seed according to claim 24, 25 or 26, wherein the 1,2,4-triazolo[1,5-a]pyrimidine-2-sulfonamide herbicide is 5,7-dimethyl-N-(2,6-dichlorophenyl)-1,2,4-triazolo[1,5-a]pyrimidine-2-sulfonamide.

28. A seed according to claim 24, 25 or 26, wherein the plant is a cereal.

29. A seed according to claim 24, 25 or 26, wherein the plant is selected from the group consisting of rice, wheat, barley, sorghum, oats, rye and millet.

30. A monocotyledonous seed from which a plant can be grown, the growth of which plant is resistant to inhibition by an herbicide at levels which normally inhibit the growth of that species of plant by inhibiting the activity of acetohydroxyacid synthase, wherein said resistance is conferred by an altered acetohydroxyacid synthase whose activity is resistant to inhibition by said herbicide at levels of said herbicide which normally inhibit the activity of an unaltered acetohydroxyacid synthase, and wherein the plant is of a species in which fertile plants can be regenerated from tissue culture.

31. A seed according to claim 30, wherein the plant is a cereal.

32. A seed according to claim 30, wherein the plant is selected from the group consisting of rice, wheat, barley, sorghum, oats, rye and millet.

33. A monocotyledonous plant, the growth of which is resistant to inhibition by a 2-(2-imidazolin-2-yl)pyridine herbicide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, and wherein the plant is of a species in which fertile plants can be regenerated from tissue culture.

34. A plant according to claim 33, wherein the 2-(2-imidazolin-2-yl)pyridine herbicide is AC 263,499.

35. A plant according to claim 33, wherein the 2-(2-imidazolin-2-yl)pyridine herbicide is AC 243,997.

36. A plant according to claim 33, 34 or 35, wherein the plant is a cereal.

37. A plant according to claim 33, 34 or 35, wherein the plant is selected from the group consisting of rice, wheat, barley, sorghum, oats, rye and millet.

38. A monocotyledonous plant, the growth of which is resistant to inhibition by a 2-(2-imidazolin-2-yl)quinoline herbicide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, and wherein the plant is of a species in which fertile plants can be regenerated from tissue culture.

39. A plant according to claim 38, wherein the 2-(2-imidazolin-2-yl)quinoline herbicide is AC 252,214.

40. A plant according to claim 38 or 39, wherein the plant is a cereal.

41. A plant according to claim 38 or 39, wherein the plant is selected from the group consisting of rice, wheat, barley, sorghum, oats, rye and millet.

42. A monocotyledonous plant, the growth of which is resistant to inhibition by an herbicidal sulfonamide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, and wherein the plant is of a species in which fertile plants can be regenerated from tissue culture.

43. A plant according to claim 42, wherein the herbicidal sulfonamide is 2-chloro-N[(4-methoxy-6-methyl-1,3,5-triazin-2-yl)aminocarbonyl] benzenesulfonamide.

44. A plant according to claim 42 or 43, wherein the plant is a cereal.

45. A plant according to claim 42 or 43, wherein the plant is selected from the group consisting of rice, wheat, barley, sorghum, oats, rye and millet.

46. A monocotyledonous plant, the growth of which is resistant to inhibition by a 1,2,4-triazolo[1,5-a]pyrimidine-2-sulfonamide herbicide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, and wherein the plant is of a species in which fertile plants can be regenerated from tissue culture.

47. A plant according to claim 46, wherein the 1,2,4-triazolo[1,5-a]pyrimidine-2-sulfonamide herbicide is 5,7-dimethyl-N-(2,5-dichlorophenyl)-1,2,4-triazolo[1,5-a]pyrimidine-2-sulfonamide.

48. A plant according to claim 46 or 47, wherein the plant is a cereal.

49. A plant according to claim 46 or 47, wherein the plant is selected form the group consisting of rice, wheat, barley, sorghum, oats, rye and millet.

50. A monocotyledonous plant, the growth of which is resistant to inhibition by a 2-(2-imidazolin-2-yl)pyridine herbicide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, wherein the growth of said plant is sensitive to inhibition by an herbicidal sulfonamide, or an herbicidal derivative thereof, at levels which normally inhibit the growth of that species of plant by inhibiting the activity of acetohydroxyacid synthase, and wherein the plant is of a species in which fertile plants can be regenerated from tissue culture.

51. A plant according to claim 50, wherein the 2-(2-imidazolin-2-yl)pyridine herbicide is AC 263,499.

52. A plant according to claim 50, wherein the 2-(2-imidazolin-2-yl)pyridine herbicide is AC 243,997.

53. A plant according to claim 50, 51 or 52, wherein the herbicidal sulfonamide is 2-chloro-N[(4-methoxy-6-methyl-1,3,5-triazin-2-yl)aminocarbonyl] benzenesulfonamide.

54. A plant according to claim 50, 51 or 52, wherein the plant is a cereal.

55. A plant according to claim 50, 51 or 52, wherein the plant is selected from the group consisting of rice, wheat, barley, sorghum, oats, rye and millet.

56. A monocotyledonous plant, the growth of which is resistant to inhibition by a 2-(2-imidazolin-2-yl)pyridine herbicide, or an herbicidal derivative thereof, at levels which normally inhibit the growth of that species of plant by inhibiting the activity of acetohydroxyacid synthase, wherein said resistance is conferred by an altered acetohydroxyacid synthase whose activity is resistant to inhibition by said herbicide or derivative at levels of said herbicide or derivative which normally inhibit the activity of an unaltered acetohydroxyacid synthase, wherein the growth of said plant is sensitive to inhibition by a 1,2,4-triazolo[1,5-a]pyrimidine-2-sulfonamide herbicide, or an herbicidal derivative thereof, at levels which normally inhibit the growth of that species of plant by inhibiting the activity of acetohydroxyacid synthase, and wherein the plant is of a species in which fertile plants can be regenerated from tissue culture.

57. A plant according to claim 56, wherein the 2-(2-imidazolin-2-yl)pyridine herbicide is AC 263,499.

58. A plant according to claim 56, wherein the 2-(2-imidazolin-2-yl)pyridine herbicide is AC 243,997.

59. A plant according to claim 56, 57 or 58, wherein the 1,2,4-triazolo[1,5-a]pyrimidine-2-sulfonamide herbicide is 5,7-dimethyl-N-(2,6-dichlorophenyl)-1,2,4-triazolo[1,5-a]pyrimidine-2-sulfonamide.

60. A plant according to claim 56, 57 or 58, wherein the plant is a cereal.

61. A plant according to claim 56, 57 or 58, wherein the plant is selected from the group consisting of rice, wheat, barley, sorghum, oats, rye and millet.

62. A monocotyledonous plant, the growth of which is resistant to inhibition by an herbicide at levels which normally inhibit the growth of that species of plant by inhibiting the activity of acetohydroxyacid synthase, wherein said resistance is conferred by an altered acetohydroxyacid synthase whose activity is resistant to inhibition by said herbicide at levels of said herbicide which normally inhibit the activity of an unaltered acetohydroxyacid synthase, and wherein the plant is of a species in which fertile plants can be regenerated from tissue culture.

63. A plant according to claim 62, wherein the plant is a cereal.

64. A plant according to claim 62, wherein the plant is selected from the group consisting of rice, wheat, barley, sorghum, oats, rye and millet.

* * * * *